United States Patent
Nishijima

(10) Patent No.: US 12,257,089 B2
(45) Date of Patent: Mar. 25, 2025

(54) DETECTOR MODULE, X-RAY COMPUTED TOMOGRAPHY APPARATUS AND X-RAY DETECTION DEVICE

(71) Applicant: Canon Medical Systems Corporation, Otawara (JP)

(72) Inventor: Akira Nishijima, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 231 days.

(21) Appl. No.: 17/936,124

(22) Filed: Sep. 28, 2022

(65) Prior Publication Data

US 2023/0106633 A1    Apr. 6, 2023

(30) Foreign Application Priority Data

Oct. 5, 2021    (JP) .................................. 2021-164178

(51) Int. Cl.
  *G01T 1/24*    (2006.01)
  *A61B 6/03*    (2006.01)
  *A61B 6/42*    (2024.01)

(52) U.S. Cl.
  CPC ............ *A61B 6/4208* (2013.01); *A61B 6/032* (2013.01); *G01T 1/24* (2013.01)

(58) Field of Classification Search
  CPC .......... A61B 6/4208; A61B 6/032; G01T 1/24
  See application file for complete search history.

(56) References Cited

U.S. PATENT DOCUMENTS

| | | | |
|---|---|---|---|
| 6,002,134 A | 12/1999 | Lingren | |
| 6,046,454 A | 4/2000 | Lingren et al. | |
| 6,333,504 B1 | 12/2001 | Lingren et al. | |
| 10,312,292 B2 * | 6/2019 | Heo | ........................ C09K 11/88 |
| 2002/0079456 A1 | 6/2002 | Lingren et al. | |
| 2007/0290142 A1 | 12/2007 | Du et al. | |
| 2014/0319363 A1 | 10/2014 | Engel et al. | |

FOREIGN PATENT DOCUMENTS

| | | | | |
|---|---|---|---|---|
| JP | 2003-279653 A | 10/2003 | | |
| JP | 2009-018154 A | 1/2009 | | |
| JP | 2009-530792 A | 8/2009 | | |
| WO | WO 2007/111822 A2 | 10/2007 | | |
| WO | WO-2020193283 A1 * | 10/2020 | ............. | G01T 1/244 |

OTHER PUBLICATIONS

Extended European Search Report issued on Feb. 2, 2023 in European Application No. 22198863.7, 7 pages.

* cited by examiner

*Primary Examiner* — Dani Fox
*Assistant Examiner* — Fani Polyzos Boosalis
(74) *Attorney, Agent, or Firm* — Oblon, McClelland, Maier & Neustadt, L.L.P.

(57) ABSTRACT

According to one embodiment, a detector module includes a direct-conversion semiconductor crystal, a first electrode provided on a first surface side of the semiconductor crystal, and a plurality of second electrodes provided on a second surface side of the semiconductor crystal opposite to the first electrode with the semiconductor crystal therebetween. The first electrode includes a first partial electrode and a second partial electrode which are applied with a high voltage independently of each other and divided at least in a channel direction.

11 Claims, 15 Drawing Sheets

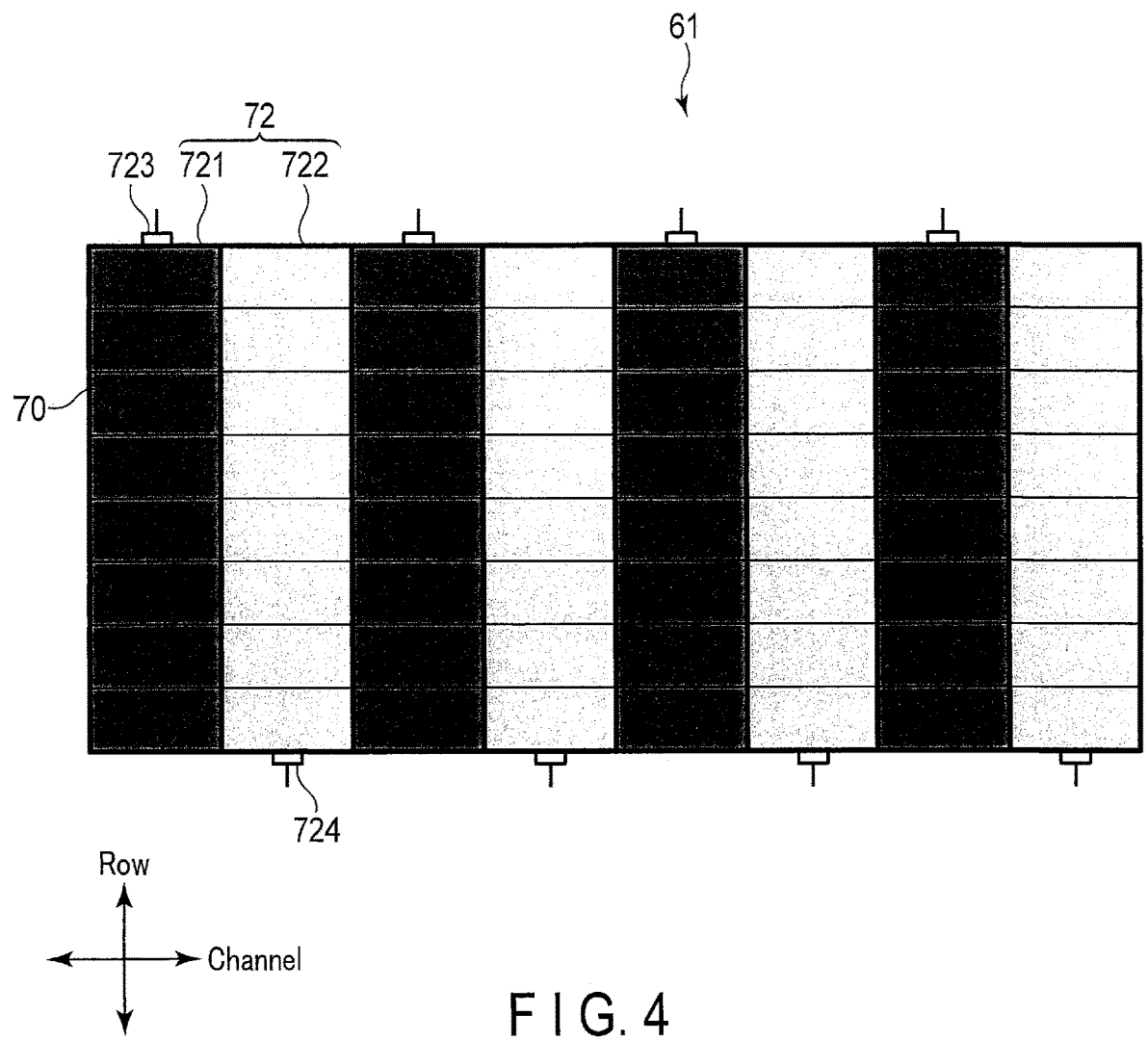
F I G. 4

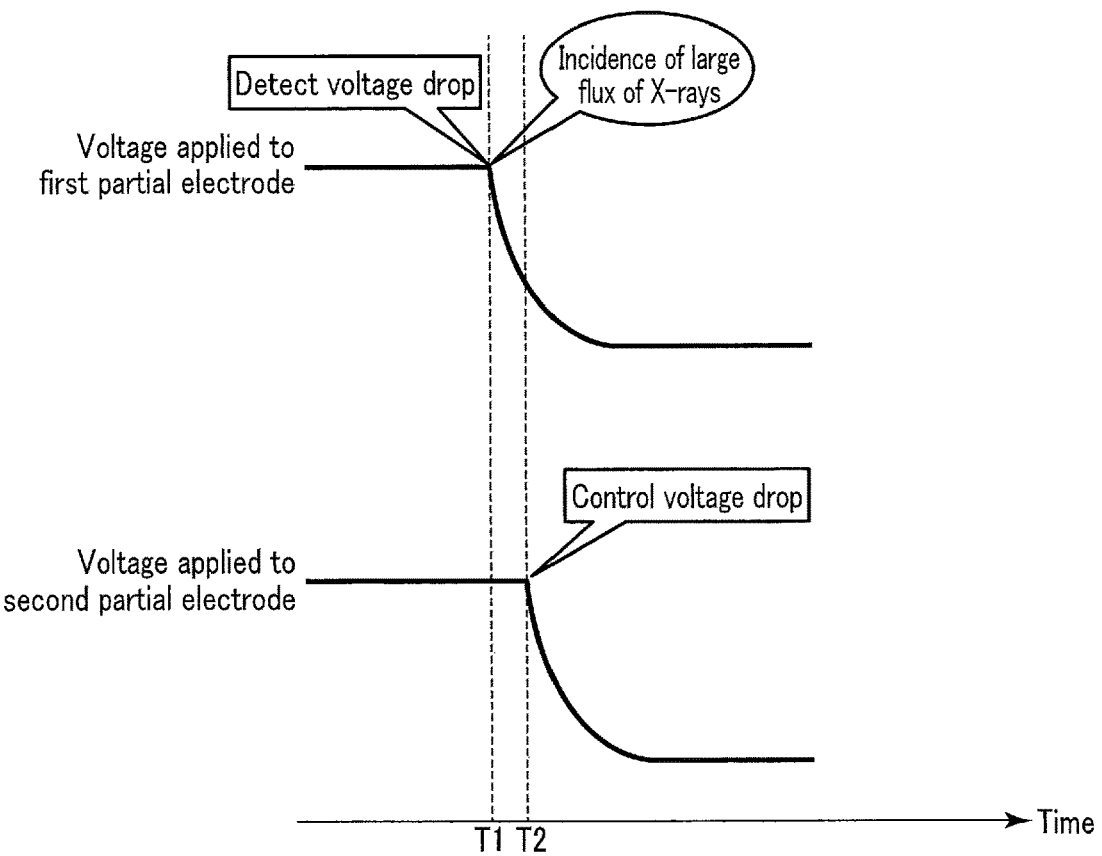
F I G. 11
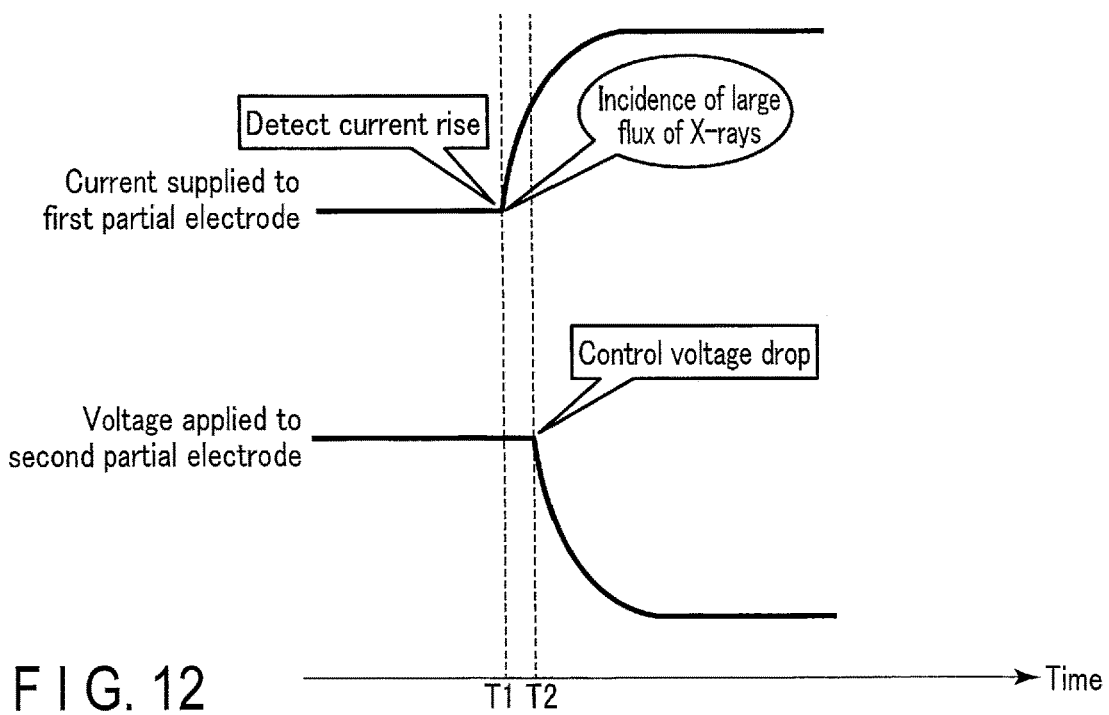
F I G. 12

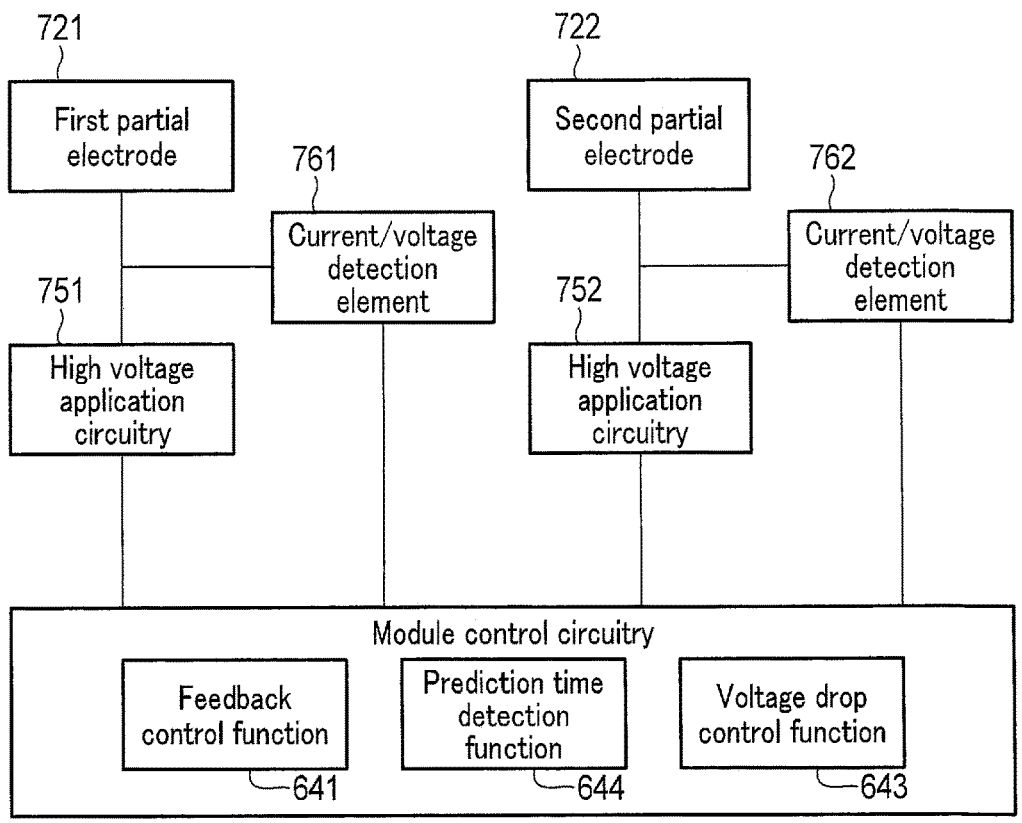
F I G. 14
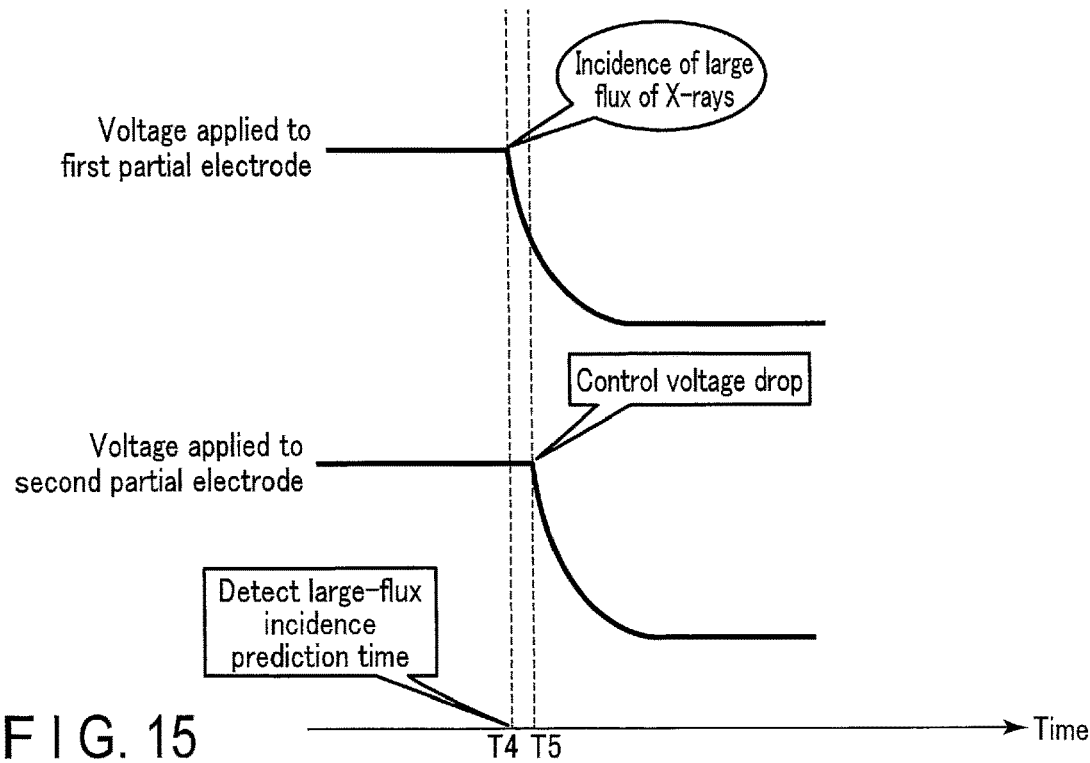
F I G. 15

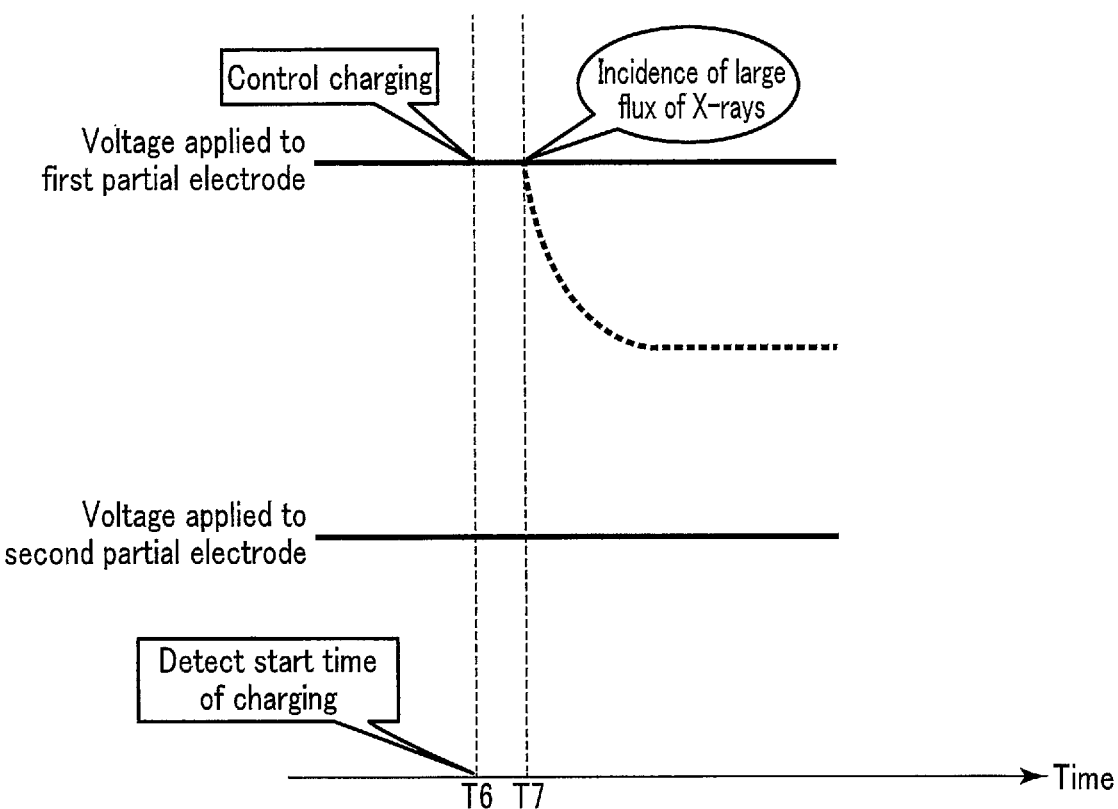
F I G. 17
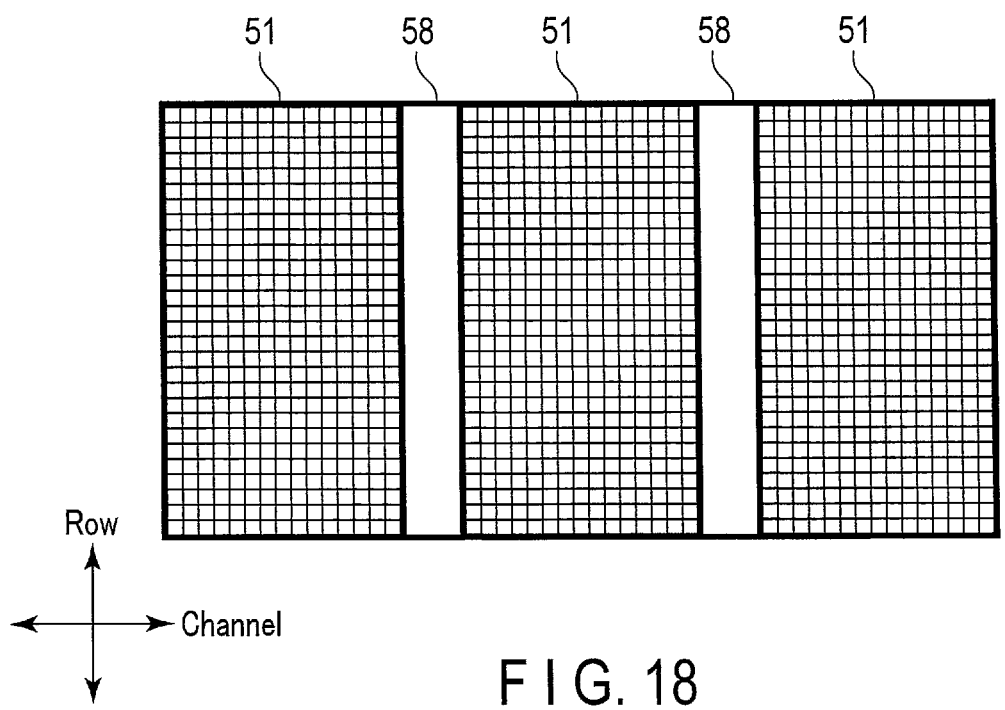
F I G. 18

DETECTOR MODULE, X-RAY COMPUTED TOMOGRAPHY APPARATUS AND X-RAY DETECTION DEVICE

CROSS-REFERENCE TO RELATED APPLICATION

This application is based upon and claims the benefit of priority from prior Japanese Patent Application No. 2021-164178, filed Oct. 5, 2021, the entire contents of which are incorporated herein by reference.

FIELD

Embodiments described herein relate generally to a detector module, an X-ray computed tomography apparatus and an X-ray detection device.

BACKGROUND

A high voltage electrode is stuck on the X-ray incident surface side of a direct-conversion semiconductor crystal, and a pixel electrode is stuck on the opposite side of the high voltage electrode with the semiconductor crystal therebetween. A high voltage is applied to the high voltage electrode. The high voltage electrode is divided in the row direction because the capability of current supply to the semiconductor crystal is improved and it is easily stuck on the semiconductor crystal.

When X-rays enter the semiconductor crystal, charges the amount of which corresponds to the flux of X-rays are generated in the semiconductor crystal. When a large flux of X-rays instantaneously enters the semiconductor crystal to generate charges the amount of which exceeds the capability of the high voltage electrode to supply a current to the semiconductor crystal, the voltage applied to the high voltage electrode drops. When the voltage drops, arc discharge may occur between adjacent high voltage electrodes. When the arc discharge occurs, the high voltage electrode may fail.

BRIEF DESCRIPTION OF THE DRAWINGS

FIG. 4 is a plan view of an X-ray detection layer shown in FIG. 3.

FIG. 11 is a diagram showing an example of high voltage control performed by voltage monitoring according to example 1.

FIG. 12 is a diagram showing an example of high voltage control performed by current monitoring according to example 1.

FIG. 14 is a block diagram showing a configuration example of a power control system related to a high voltage electrode according to example 2 of the second embodiment.

FIG. 15 is a diagram showing an example of high voltage control according to example 2 of the second embodiment.

FIG. 17 is a diagram showing an example of high voltage control according to example 3 of the second embodiment.

FIG. 18 is a diagram showing an example of arrangement of detector modules according to a third embodiment.

DETAILED DESCRIPTION

Figure 1:
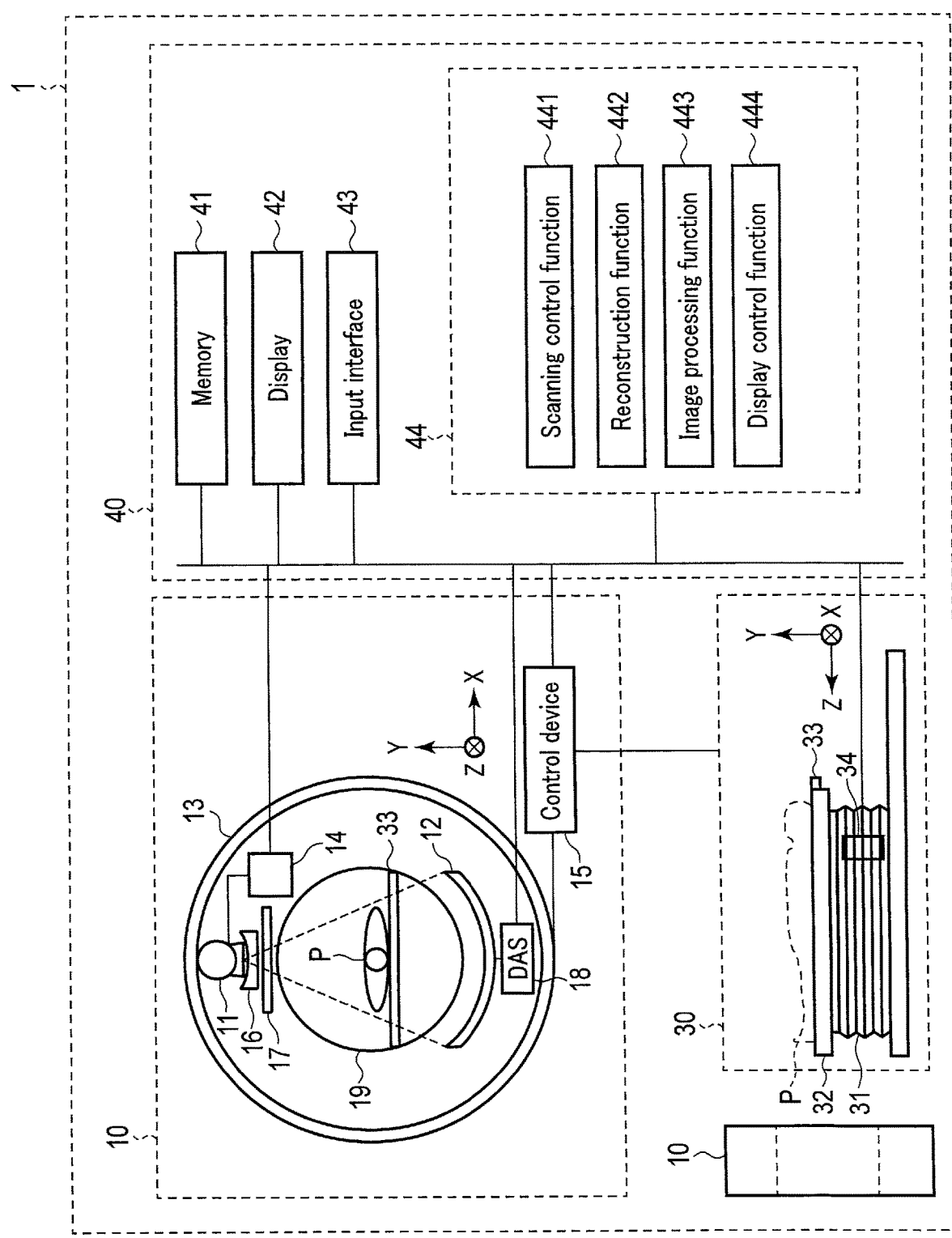
FIG. 1 is a diagram showing a configuration example of an X-ray computed tomography apparatus according to a first embodiment.

A detector module according to one embodiment includes a direct-conversion semiconductor crystal, a first electrode provided on a first surface side of the semiconductor crystal, and a plurality of second electrodes provided on a second surface side of the semiconductor crystal opposite to the first electrode with the semiconductor crystal therebetween, and the first electrode includes a first partial electrode and a second partial electrode which are independently applied with a high voltage and divided at least in a channel direction.

Embodiments of a detector module, an X-ray computed tomography apparatus and an X-ray detection device will be described below in detail with reference to the accompanying drawings. In the following description, the components having the same or substantially the same function are denoted by the same sign with respect to the drawings and their descriptions will be repeated only when necessary. Even though the components shown in the drawings are the same, their dimensions and ratios may vary from drawing to drawing.

There are a variety of types of X-ray computed tomography apparatus (X-ray CT apparatus) such as a third-generation CT and a fourth-generation CT, and any of the types is applicable to the embodiments. The third-generation CT is of a rotate/rotate-type in which an X-ray tube and a detector rotate integrally around a subject. The fourth-generation CT is of a stationary/rotate-type in which a large number of X-ray detection elements arrayed in a ring shape are fixed and only the X-ray tube rotates around a subject.

First Embodiment

FIG. 1 is a diagram showing a configuration example of an X-ray computed tomography apparatus 1 according to a first embodiment. As shown in FIG. 1, the X-ray computed tomography apparatus 1 includes a gantry 10, a bed 30 and a console 40. For convenience of description, a plurality of gantries 10 are shown in FIG. 1, but the number of gantries 10 may be one or plural. The gantry 10 is a scanner configured to perform X-ray CT scanning on the subject P. The bed 30 is a conveyance device on which the subject P is placed as a target of X-ray CT scanning and which is used to position the subject P. The console 40 is a computer that controls the gantry 10. For example, the gantry 10 and bed 30 are installed in a CT examination room, and the console 40 is installed in a control room adjacent to the CT examination room. The gantry 10, bed 30 and console 40 are connected communicably by wire or by radio. Note that the console 40 may not necessarily be installed in the control room. For example, the console 40 may be installed in the same room as the gantry 10 and bed 30. Besides, the console 40 may be built in the gantry 10.

As shown in FIG. 1, the gantry 10 includes an X-ray tube 11, an X-ray detector 12, a rotation frame 13, an X-ray high voltage device 14, a control device 15, a wedge 16, a collimator 17 and a data acquisition circuitry (data acquisition system: DAS) 18.

The X-ray tube 11 irradiates the subject P with X-rays. Specifically, the X-ray tube 11 includes a cathode which generates thermions, an anode which receives the thermions from the cathode to generate X-rays, and a vacuum tube which holds the cathode and anode. The X-ray tube 11 is connected to the X-ray high voltage device 14 via a high voltage cable. A tube voltage is applied between the cathode and anode by the X-ray high voltage device 14. By the application of the tube voltage, thermions fly from the cathode toward the anode. When the thermions fly from the cathode toward the anode, a tube current flows. The thermions impinging on the anode to generate X-rays.

The X-ray detector 12 detects in units of photons X-rays which are radiated from the X-ray tube 11 and transmitted through the subject P, and outputs to the DAS 18 an electrical signal having a peak corresponding to the number of photons of the incident X-rays. The X-ray detector 12 has, for example, a configuration in which a plurality of pixel arrays are arranged in a slice direction (row direction) and the pixel arrays each include a plurality of detector elements arranged in a channel direction along one arc with the focal point of the X-ray tube 11 centered. The channel direction and the row direction are orthogonal to each other. The X-ray detector 12 is a direct-conversion detector.

The rotation frame 13 is an annular frame which supports the X-ray tube 11 and X-ray detector 12 such that they can be rotated around a rotation axis (Z-axis). Specifically, the rotation frame 13 supports the X-ray tube 11 and X-ray detector 12 such that they are opposed to each other. Note that the rotation frame 13 also supports the X-ray high voltage device 14 and DAS 18 in addition to the X-ray tube 11 and X-ray detector 12. The rotation frame 13 is supported on a stationary frame (not shown) rotatably around the rotation axis. The rotation frame 13 has a rotation mechanism including, for example, a motor that generates a rotational driving force and a bearing that transmits the rotation driving force to the rotation frame 13 to rotate it. The motor is provided on a stationary frame, the bearing is physically connected to the rotation frame 13 and the motor, and the rotation frame 13 is rotated in accordance with the rotational force of the motor. When the rotation frame 13 rotates around the rotation axis, the X-ray tube 11 and X-ray detector 12 rotate around the rotation axis. The rotation frame 13 is an example of a rotation unit.

The first embodiment is applicable to decubitus CT and/or upright CT. In the decubitus CT, the longitudinal direction of the rotation axis of the rotation frame 13 in a non-tilt state or the table top 33 of the bed 30 will be defined as a Z-axis direction, a direction orthogonal to the Z-axis direction and horizontal to the floor surface will be defined as an X-axis direction, and a direction orthogonal to the Z-axis direction and perpendicular to the floor surface will be defined as a Y-axis direction. When the first embodiment is applicable only to the upright CT or to both the decubitus CT and upright CT, the longitudinal direction of the rotation axis of the rotation frame 13 in a non-tilt state will be defined as a Z-axis direction, a direction orthogonal to the Z-axis direction and from the center of rotation to a support row supporting the rotation frame 13 will be defined as an X-axis direction, and a direction orthogonal to the Z-axis direction and the X-axis direction will be defined as a Y-axis direction.

The X-ray high voltage device 14 includes a high voltage generator and an X-ray controller. The high voltage generator includes a transformer and an electric circuitry such as a rectifier to generate a high voltage to be applied to the X-ray tube 11 and a filament current to be supplied to the X-ray tube 11. The X-ray controller controls an output voltage corresponding to X-rays radiated from the X-ray tube 11. The high voltage generator may be of a transformer type or an inverter type. The X-ray high voltage device 14 may be provided in the rotation frame 13 in the gantry 10 or may be provided in the stationary frame (not shown) in the gantry 10.

The wedge 16 adjusts the dose of X-rays with which the subject P is irradiated. Specifically, the wedge 16 attenuates X-rays radiated from the X-ray tube 11 onto the subject P such that the dose of the X-rays may have a predetermined distribution. As the wedge 16, for example, a metal plate of aluminum or the like, such as a wedge filter and a bow-tie filter, is used.

The collimator 17 restricts the range of radiation of X-rays which have been transmitted through the wedge 16. The collimator 17 slidably supports a plurality of lead plates which shield X rays and adjusts the form of a slit that is formed by the lead plates. Note that the collimator 17 may also be referred to as an X-ray diaphragm.

The data acquisition circuitry 18 processes electrical signals supplied from the X-ray detector 12 to count the number of photons of X-rays for each view. The data acquisition circuitry 18 acquires count data having a digital value representing the number of photons for each view. The count data is called detection data. The data acquisition circuitry 18 is implemented by an application specific integrated circuitry (ASIC) on which circuitry elements capable of generating count data are mounted. The count data is transmitted to the console 40 via a non-contact data transmission device or the like.

Although the photon counting-type X-ray detector 12 and data acquisition circuitry 18 are each described as an example in the first embodiment, the technique according to the first embodiment may also be applied to an integral-type X-ray detector and a data acquisition circuitry.

The rotation frame 13 and the stationary frame are each provided with a non-contact type or contact type communication circuitry to perform communications between a unit supported by the rotation frame 13 by the communication circuitry and an external device of the stationary frame or gantry 10. For example, when optical communication is employed as a non-contact communication system, detection data generated by the DAS 18 is transmitted by optical communication from a transmitter including a light emitting diode (LED) provided on the rotation frame 13 to a receiver including a photodiode and provided on the stationary frame of the frame 10, and is further transferred from the stationary frame to the console 40 by the transmitter. As the communication system, a contact-type data transmission system using a slip ring and an electrode brush may be employed in addition to a non-contact type data transmission system such as a capacitive coupling system and a radio wave system.

The control device 15 controls the X-ray high voltage device 14 and data acquisition circuitry 18 in order to execute X-ray CT scanning in accordance with a scanning control function 441 of a processing circuitry 44 of the console 40. The control device 15 includes a processing circuitry including a central processing unit (CPU), a micro processing unit (MPU) or the like, and a driving device such as a motor and an actuator. The processing circuitry includes, as hardware resources, a processor such as a CPU, and a memory such as a read only memory (ROM) and a random access memory (RAM). The control device 15 causes a processor to perform various functions to execute a program developed in the memory. Note that the various functions are not necessarily fulfilled by a single processing circuitry. A processing circuitry may be configured by combining a plurality of independent processors, and each of the processors may execute a program to fulfill each of the functions. In addition, the control device 15 may be implemented by an ASIC and a field programmable gate array (FPGA). The control device 15 may also be implemented by a complex programmable logic device (CPLD) or a simple programmable logic device (SPLD).

The control device 15 has a function of receiving an input signal from an input interface 43 (described later) which is attached to the console 40 or the gantry 10 to control the operation of the gantry 10 and bed 30. For example, upon receiving an input signal, the control device 15 performs control to rotate the rotation frame 13, to tilt the gantry 10 and to move the bed 30 and table top 33. The control to tilt the gantry is achieved by the control device 15 rotating the rotation frame 13 around the axis parallel to the X-axis direction based on tilt angle information input from the input interface attached to the gantry 10. Note that the control device 15 may be provided in the gantry 10 and the console 40.

The bed 30 includes a base 31, a support frame 32, the table top 33 and a bed driving device 34. The base 31 is installed on the floor surface. The base 31 is a housing which supports the support frame 32 movably in a direction (Y-axis direction) perpendicular to the floor surface. The support frame 32 is a frame provided on an upper part of the base 31. The support frame 32 supports the table top 33 slidably along the rotation axis (Z-axis). The table top 33 is a plate with flexibility, on which the subject P is placed.

The bed driving device 34 is housed in the bed 30. The bed actuator 34 is a motor or an actuator which generates driving force to move the table top 33 and the support frame 32 on which the subject P is placed. The bed driving device 34 operates under the control of the console 40 and the like.

The console 40 includes a memory 41, a display 42, an input interface 43 and a processing circuitry 44. Data communication between the memory 41, display 42, input interface 43 and processing circuitry 44 is performed via a bus. Although the console 40 is described as being separated from the gantry 10, the console 40 or some components thereof may be included in the gantry 10.

The memory 41 is a storage device which stores various information items, such as a hard Disk Drive (HDD), a solid state drive (SSD) and an integrated circuitry storage device. The memory 41 may be, aside from the HDD, SSD and the like, a portable storage medium such as a compact disc (CD), a digital versatile disc (DVD), a blue-ray (registered trademark) disc (BD) and a flash memory. The memory 41 may also be a driving device which reads and writes various information items between semiconductor memory elements such as a flash memory and a RAM. In addition, the storage area of the memory 41 may exist in the X-ray computed tomography apparatus 1 and an external storage device connected over a network. The memory 41 stores, for example, projection data and reconstructed image data.

The display 42 displays various kinds of information. The display 42 outputs a CT image generated by the processing circuitry 44, a graphical user interface (GUI) for accepting various operations from an operator, and the like. Various optional displays can appropriately be used as the display 42. For example, a liquid crystal display (LCD), a cathode ray tube (CRT) display, an organic electro luminescence display (OELD), and a plasma display can be used as the display 42.

Note that the display 42 may be provided anywhere in the control room. In addition, the display 42 may be a desktop display, or may be configured as, for example, a tablet terminal capable of wireless communication with the main body of the console 40. As the display 42, one or more projectors may be used.

The input interface 43 receives various input operations from the operator, converts the accepted input operations into electrical signals, and outputs them to the processing circuitry 44. For example, the input interface 43 receives from the operator an acquisition condition for acquiring projection data, a reconstruction condition for reconstructing a CT image, an image processing condition for generating a post-processed image from the CT image, and the like. As the input interface 43, for example, use can be made of, as appropriate, a mouse, a keyboard, a trackball, a switch, a button, a joystick, a touchpad, a touch panel display, etc. Note that in the first embodiment, the input interface 43 is not limited to a device including a physical operating component such as a mouse, a keyboard, a trackball, a switch, a button, a joystick, a touchpad and a touch panel display. Examples of the input interface 43 include a circuitry for receiving an electrical signal corresponding to an input operation from an external input device which is provided separately from the device, and processing the electrical signal to be output to the processing circuitry 44. The input interface 43 may also be provided on the gantry 10. The input interface 43 may also be configured by a tablet terminal or the like capable of wireless communication with the main body of the console 40.

The processing circuitry 44 controls the operation of the X-ray computed tomography apparatus 1 in its entirety in accordance with an electrical signal of an input operation output from the input interface 43. The processing circuitry 44 generates image data based on an electrical signal output from the X-ray detector 12. For example, the processing circuitry 44 includes, as hardware resources, a processor such as a CPU, an MPU and a GPU, and a memory such as a ROM and a RAM. The processing circuitry 44 causes the processor, which executes a program developed on the memory, to perform a scanning control function 441, a reconstruction function 442, an image processing function 443, a display control function 444, and the like.

Note that each of the functions 441 to 444 is not necessarily fulfilled by a single processing circuitry. A processing circuitry may be configured by combining a plurality of independent processors, and each of the processors may fulfill each of the functions 441 to 444.

In the scanning control function 441, the processing circuitry 44 controls the X-ray high voltage device 14, control device 15 and DAS 18 to perform X-ray CT scanning in accordance with scanning conditions. In the reconstruction function 442, the processing circuitry 44 applies preprocesses, such as a logarithmic conversion process, an offset correction process, an inter-channel sensitivity correction process and beam hardening correction, to the count data that is output from the DAS 18. The processing circuitry 44 performs a reconstruction process for the preprocessed count data using a filtered back projection method, an iterative approximation reconstruction method, machine learning and the like to generate a CT image. In the image processing function 443, the processing circuitry 44 converts the CT image, which is generated by the reconstruction function 442, into a section image of a selected section or a rendered image in a selected viewpoint direction. The conversion is performed based on an input operation which was received from the operator via the input interface 43. For example, the processing circuitry 44 performs three-dimensional image processing, such as volume rendering, surface volume rendering, an image value projecting process, a multi-planer reconstructing process, and a curved MPR (CPR) process, for the CT image data to generate a rendered image in a selected viewpoint direction. The generation of rendered image data in the selected viewpoint direction may be performed directly by the reconstruction function 442. In the display control function 444, the processing circuitry 44 displays various images, which are generated by the image processing function 443, on the display 42. For example, a CT image, a section image of a selected section, a rendered image in a selected viewpoint direction, a setting screen of scanning conditions, and the like are displayed on the display 42.

Note that it has been described that the console 40 performs a plurality of functions as a single console, but different consoles may perform a plurality of functions. The processing circuitry 44 may not necessarily be included in the console 40, and may be included in an integrated server which collectively performs a process on projection data obtained by a plurality of medical diagnostic imaging devices. The post-processing may be performed by the console 40 or an external workstation. It may also be performed by both the console 40 and the external workstation at the same time.

The overall configuration of the X-ray computed tomography apparatus 1 according to the first embodiment has been described. Next is a detailed description of the X-ray detection device according to the first embodiment. The X-ray detection device is a mechanical device including the X-ray detector 12 and DAS 18.

Figure 2:
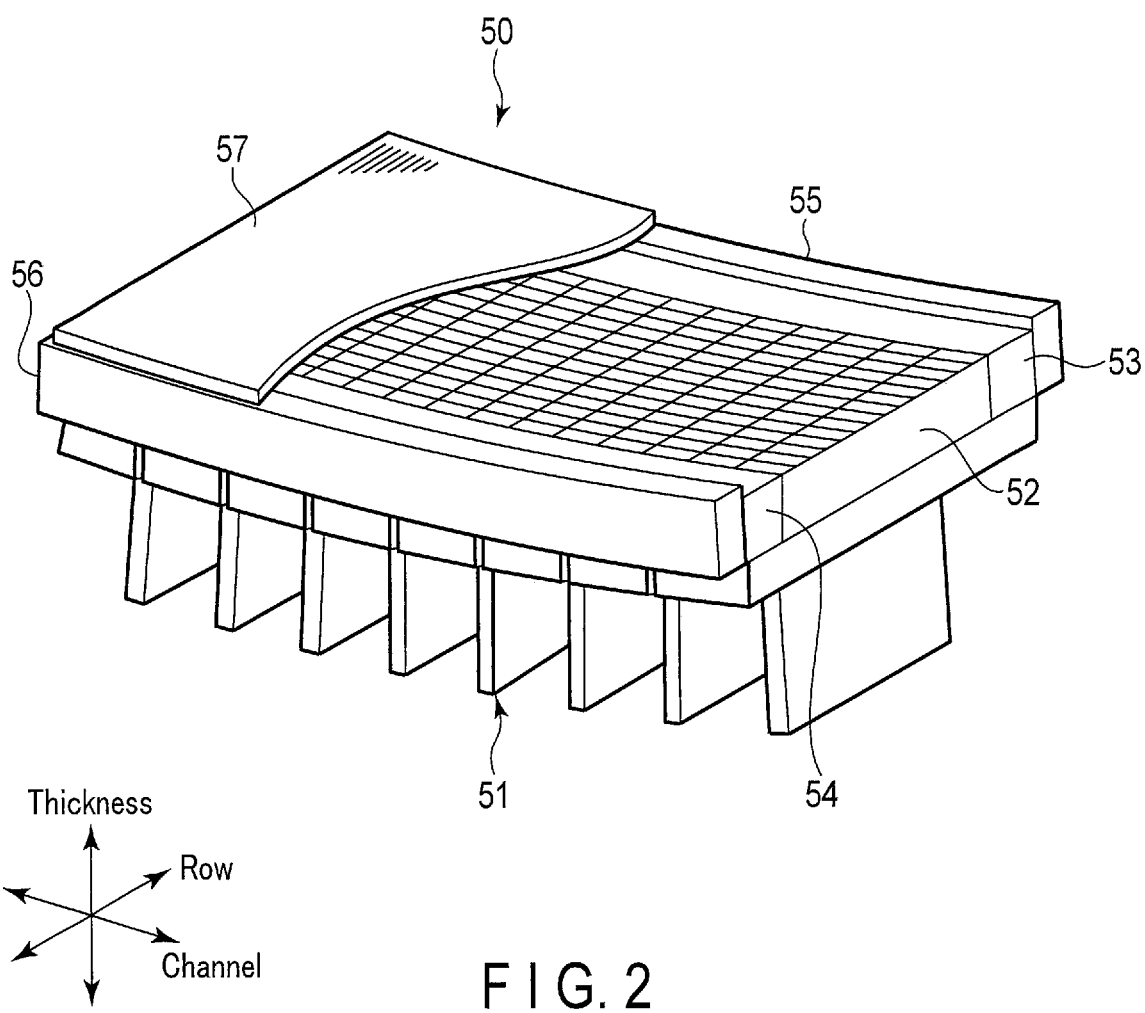
FIG. 2 is a schematic perspective view showing a configuration of an X-ray detection device.

FIG. 2 is a schematic perspective view showing a configuration of an X-ray detection device 50. As shown in FIG. 2, the X-ray detection device 50 includes a detector module 51, a collimator 52, a first stationary frame 53, a second stationary frame 54, a first support frame 55, a second support frame 56 and a light-shielding plate 57. Note that a direction orthogonal to the channel direction and the row direction is referred to as a thickness direction.

The detector module 51 is a mechanical device including the X-ray detector 12 and DAS 18. In the X-ray detection device 50, a plurality of detector modules 51 are arranged along the channel direction.

The collimator 52 includes a plurality of collimator plates arranged in a lattice to limit a solid angle of X-rays incident upon detector pixels of each of the detector modules 51. Specifically, the collimator 52 removes X-rays scattered by various structures such that only X-rays directly enter the detector pixels. The collimator 52 is formed in a substantially arc shape along the channel direction and placed to cover an X-ray detection layer 61 of each of the detector modules 51.

The first and second stationary frames 53 and 54 fix the positions of the detector modules 51 such that the detector modules 51 are aligned in the channel direction. The first and second support frames 55 and 56 support the collimator 52 and the first and second stationary frames 53 and 54. Specifically, the first and second support frames 55 and 56 support the collimator 52 and the first and second stationary frames 53 and 54 to sandwich them from both sides in the row direction. The light-shielding plate 57 reduces light incident upon the X-ray detection layer 61 of the detector modules 51. For example, the light-shielding plate 57 is a member formed in a thin plate shape using a material capable of reducing light. The light-shielding plate 57 is attached to the first and second support frames 55 and 56 so as to cover the whole of the collimator 52.

Figure 3:
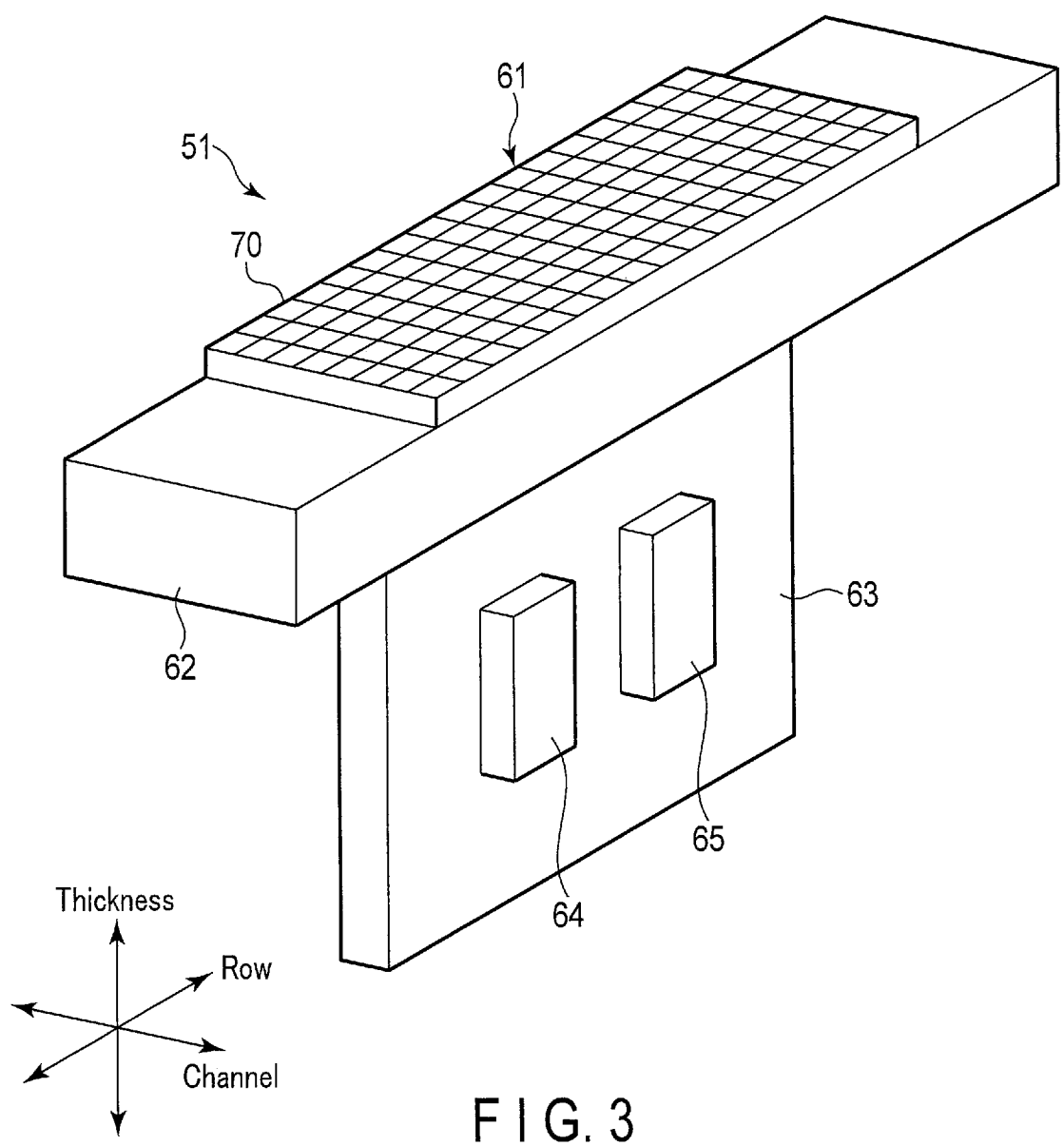
FIG. 3 is a schematic perspective view showing a configuration of a detector module.

FIG. 3 is a schematic perspective view showing a configuration of the detector modules 51. As shown in FIG. 3, each of the detector modules 51 includes an X-ray detection layer 61, a support base 62, a control board 63, a module control circuitry 64 and a DAS circuitry 65. The X-ray detection layer 61 includes a plurality of detector pixels 70 arranged in the channel direction and the row direction. Each of the detector pixels 70 detects an incident X-ray. The X-ray detection layers 61 of the detector modules 51 constitute an X-ray detector 12. The support base 62 is a structure that supports the X-ray detection layer 61 including a plurality of detector pixels 70. The control board 63 is connected to the support base 62. The control board 63 is provided with the module control circuitry 64 and the DAS circuitry 65. The module control circuitry 64 is an integrated circuitry that controls an electrical system provided in the X-ray detection layer 61. The DAS circuitry 65 is an integrated circuitry that collects count data through the detector pixels 70. The DAS circuitry 65 of the detector modules 51 constitute the DAS 18.

Figure 5:
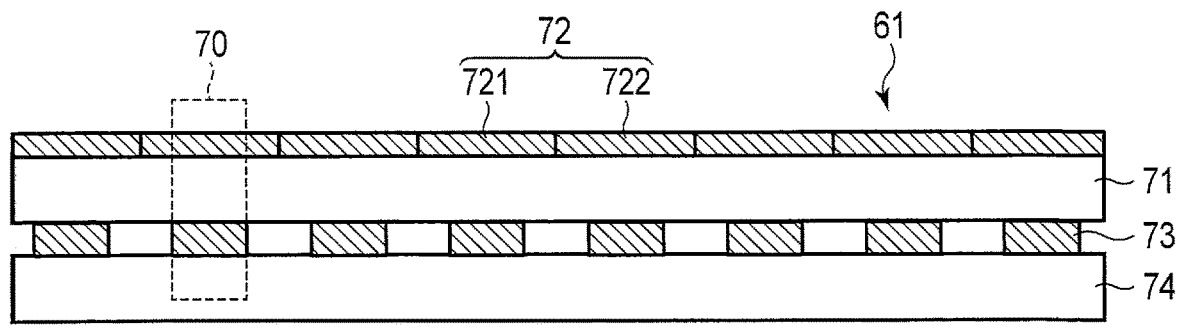
FIG. 5 is a sectional view of the X-ray detection layer shown in FIG. 3.

FIG. 4 is a plan view of the X-ray detection layer 61 shown in FIG. 3, and FIG. 5 is a sectional view of the X-ray detection layer 61 shown in FIG. 3. The plan view of FIG. 4 is viewed from the X-ray tube 11 to the X-ray detection device 50, and the sectional view of FIG. 5 corresponds to a two-dimensional plane defined by the row and channel directions.

As shown in FIG. 5, the X-ray detection layer 61 includes a direct-conversion semiconductor crystal 71. As the semiconductor crystal 71, for example, amorphous selenium, zinc iodide, cadmium telluride, cadmium zinc telluride, or any other semiconductor material has only to be used. When X-rays enter the semiconductor crystal 71, charges are generated to correspond to the flux of the X-rays or the number of photons thereof. High voltage electrodes 72 are provided on the X-ray entering surface of the semiconductor crystal 71. A high voltage application circuitry to be described later applies a high voltage to move the charges to the pixel electrodes 73. The high voltage application circuitry applies power to the semiconductor crystal 71 via the high voltage electrodes 72. The pixel electrodes 73 are opposed to the high voltage electrodes 72 with the semiconductor crystal 71 therebetween. A DAS circuitry 65 is connected to each of the pixel electrodes 73 via a signal line. The DAS circuitry 65 collects charges, which are generated in the semiconductor crystal 71, as a current signal through the pixel electrode 73. A support substrate 74 is opposed to the semiconductor crystal 71 with the pixel electrodes 73 therebetween. The support substrate 74 is provided with the support base 62 shown in FIG. 3. The pixel electrodes 73 are in a one-to-one correspondence with the detector pixels 70.

As shown in FIGS. 4 and 5, the high voltage electrodes 72 according to the first embodiment are each divided into a plurality of partial electrodes 721 and 722 in the channel direction. Specifically, the high voltage electrodes 72 are each divided into a first partial electrode 721 and a second partial electrode 722, and the first and second partial electrodes 721 and 722 of the high voltage electrodes 72 are arranged along the channel direction. Each of the high voltage electrodes 72 is not divided in the row direction orthogonal to the channel direction. That is, the first and second partial electrodes 721 and 722 are provided so as to extend over the detector pixels 70 or pixel electrodes 73 in the row direction. A high voltage is applied to the first and second partial electrodes 721 and 722 independently of each other.

As shown in FIG. 4, each of the partial electrodes 721 and 722 is bonded to the semiconductor crystal 71 so as to cover one detector pixel 70 or pixel electrode 73 in the channel direction. That is, the width of each of the partial electrodes 721 and 722 in the channel direction corresponds to the width of one detector pixel 70 or pixel electrode in the channel direction. However, the first embodiment is not limited to this width. For example, the width of each of the partial electrodes 721 and 722 in the channel direction may be designed to correspond to the width of two or more detector pixels 70 or pixel electrodes in the channel direction.

As shown in FIG. 4, the first partial electrode 721 is provided with a terminal 723, and the terminal 723 is connected to the high voltage application circuitry via a signal line (not shown). Similarly, the second partial electrode 722 is provided with a terminal 724, and the terminal 724 is connected to the high voltage application circuitry via a signal line (not shown). A high voltage is applied to the first and second partial electrodes 721 and 722 independently of each other. A common high voltage is applied to a plurality of first partial electrodes 721 spaced apart in the channel direction. Similarly, a common high voltage is applied to a plurality of second partial electrodes 722 spaced apart in the channel direction.

Figure 6:
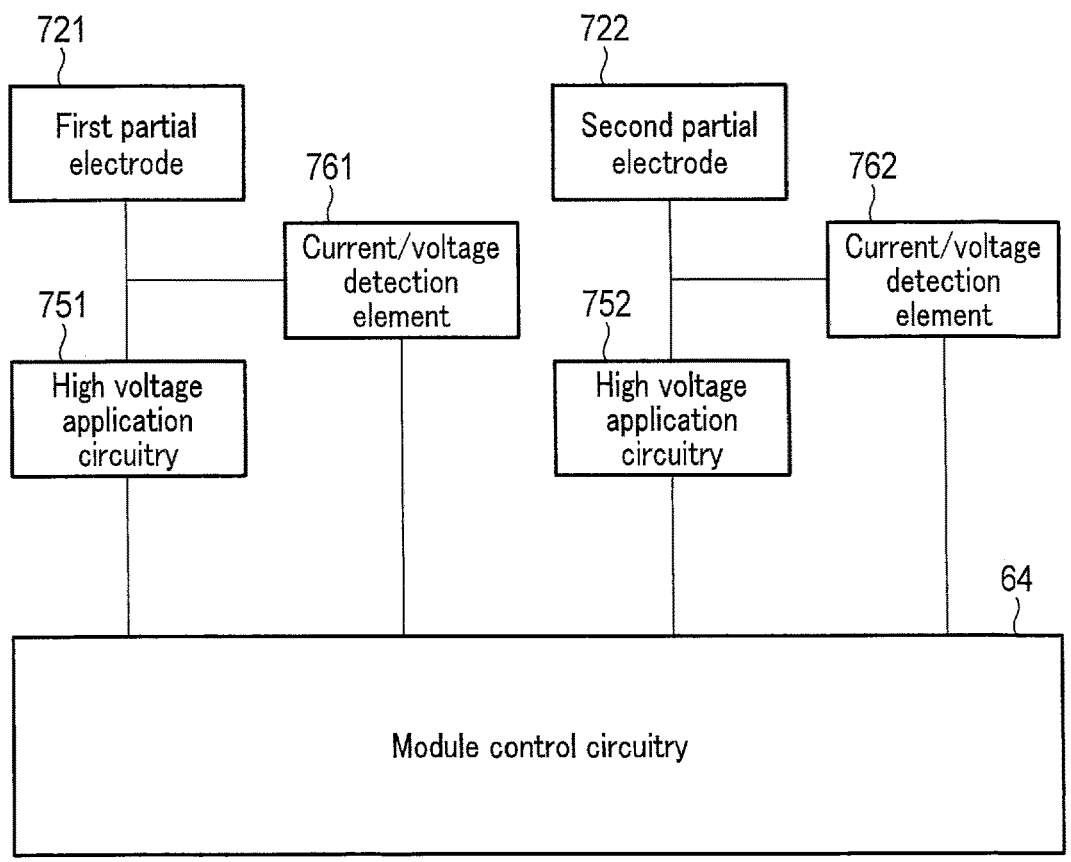
FIG. 6 is a block diagram showing a configuration example of a power control system related to a high voltage electrode.

FIG. 6 is a block diagram showing a configuration example of a power control system related to the high voltage electrode 72. As shown in FIG. 6, a high voltage application circuitry 751 is connected to the first partial electrode 721 of the high voltage electrode 72 via a signal line. A current/voltage detection element 761 is provided on a signal line connecting the first partial electrode 721 and the high voltage application circuitry 751. Each of the high voltage application circuitry 751 and the current/voltage detection element 761 is connected to the module control circuitry 64 via a signal line. Similarly, a high voltage application circuitry 752 is connected to the second partial electrode 722 of the high voltage electrode 72 via a signal line. A current/voltage detection element 762 is provided on a signal line connecting the second partial electrode 722 and the high voltage application circuitry 752. Each of the high voltage application circuitry 752 and current/voltage detection element 762 is connected to the module control circuitry 64 via a signal line.

The high voltage application circuitry 751 applies a high voltage to the first partial electrode 721 under the control of the module control circuitry 64. The high voltage is also called a bias voltage. The current/voltage detection element 761 detects a voltage applied to the first partial electrode 721 or a current supplied to the first partial electrode 721. The detected voltage will be referred to as the detected voltage, and the detected current will be referred to as the detected current. The detected voltage or the detected current is supplied to the module control circuitry 64 as an analog signal or a digital signal. Similarly, the high voltage application circuitry 752 applies a high voltage to the second partial electrode 722 under the control of the module control circuitry 64. The current/voltage detection element 762 detects a voltage applied to the second partial electrode 722 or a current supplied to the second partial electrode 722. The detected voltage or the detected current is supplied to the module control circuitry 64 as an analog signal or a digital signal.

The module control circuitry 64 is implemented by an analog or digital control circuitry. The module control circuitry 64 individually controls the high voltage application circuitry 751 and 752 to apply a high voltage to the partial electrodes 721 and 722 independently. Specifically, the module control circuitry 64 applies a high voltage having a set value to the first partial electrode 721 according to feedback control based on the detected current/detected voltage from the current/voltage detection element 761 and the target current/target voltage. Similarly, the module control circuitry 64 applies a high voltage having a set value to the second partial electrode 722 according to feedback control based on the detected current/detected voltage from the current/voltage detection element 762 and the target current/target voltage. The set values of voltages applied to the first and second partial electrodes 721 and 722 are set to the same value. In addition, the module control circuitry 64 can control the high voltage application circuitry 751 and 752 to switch the polarity of the high voltage applied to the partial electrodes 721 and 722.

Here is a description of the collection of electrical signals by the detector pixels 70. When X-rays enter the semiconductor crystal 71, charges are generated in a number proportional to the flux, dose or photon number of the X-rays. Assume in the following description that when it is unnecessary to physically distinguish the flux, dose and photon number, the term "flux" is used. The high voltage (bias voltage) applied to the high voltage electrodes 721 and 722 attracts charges to the pixel electrodes 73. More specifically, an electron/hole pair is generated in the semiconductor crystal 71, and charges corresponding to the polarity of the high voltage applied to the high voltage electrodes 721 and 722 are attracted to the pixel electrodes 73. For example, when a high voltage of negative polarity is applied, electrons are attracted to the pixel electrodes 73. The electrons attracted to the pixel electrodes 73 are read out of the pixel electrodes 73 by the DAS circuitry 65 as current signals having a peak corresponding to the flux of incident X-rays.

As described above, the high voltage electrodes 72 according to the first embodiment are each divided into a first partial electrode 721 and a second partial electrode 722 in the channel direction. This division can make the current supply capability of the detector pixels 70 higher than in the case where the number of high voltage electrodes is one.

Here is a description of the advantage of dividing the high voltage electrode 72 in the channel direction. The high voltage electrode 72 may be divided in the row direction as well as the channel direction. The difference in division between the row and channel directions appears when a large flux of X-rays enter the X-ray detection device 50.

Figure 7:
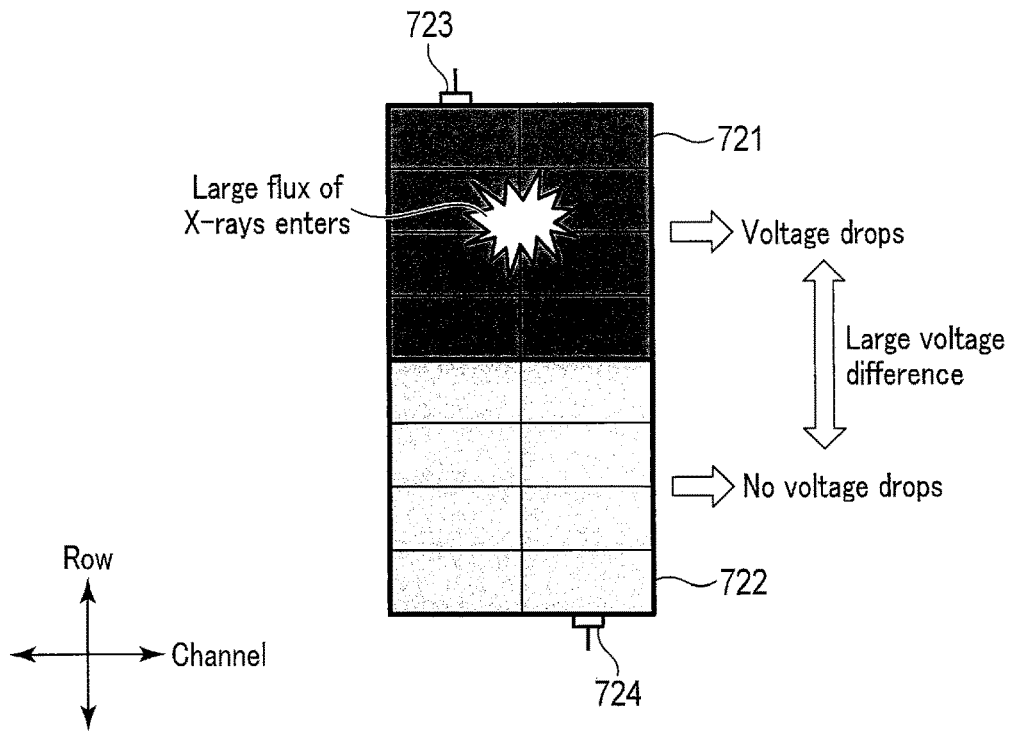
FIG. 7 is a schematic diagram showing a change in voltage when a large flux of X-rays enters an X-ray detection layer including high voltage electrodes divided in a row direction.

FIG. 7 is a schematic diagram showing a change in voltage when a large flux of X-rays enters an X-ray detection layer including a high voltage electrode 72 divided in the row direction. When X-rays enter a semiconductor crystal, charges proportional to a flux of the X-rays are generated in the semiconductor crystal. If a large flux of X-rays exceeding the charge generating ability of the semiconductor crystal instantaneously enters, the semiconductor crystal is saturated and no charges are generated in proportion to the flux of the X-rays, and therefore, current signals having a peak proportional to the flux of the X-rays cannot be collected from the pixel electrodes. Due to the saturation of the semiconductor crystal, the value of the high voltage applied to the high voltage electrode 72 decreases.

In the parietal region of the human body, the skull, which is a high X-ray absorbing portion, is located at the end of the human body. When such a portion is scanned, a phenomenon in which a large difference occurs in a flux of incident X-rays between adjacent regions, that is, a flux step occurs. When the high voltage electrodes are divided in the row direction, a large flux of X-rays does not enter a semiconductor crystal region corresponding to the second partial electrode 722 located lower in the row direction, but a large flux of X-rays instantaneously enter a semiconductor crystal region corresponding to the first partial electrode 721 located upper in the row direction. When a large flux of X-rays enters the first partial electrode 721, a voltage drops in the first partial electrode 721, but no voltage drops in the second partial electrode 722 because the first and second partial electrodes 721 and 722 are electrically separate systems. When a voltage drop occurs only in the first partial electrode 721, a voltage difference occurs between the first and second partial electrodes 721 and 722, and an arc discharge occurs between the first and second partial electrodes 721 and 722. When the arc discharge occurs, a failure is likely to occur in the first and second partial electrodes 721 and 722.

Figure 8:
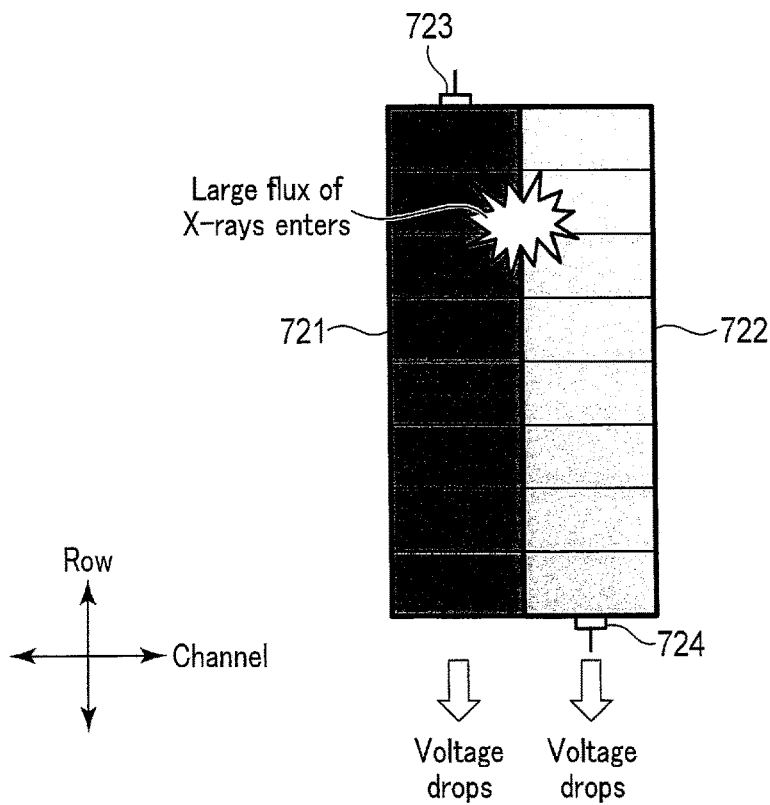
FIG. 8 is a schematic diagram showing a change in voltage when a large flux of X-rays enters an X-ray detection layer including high voltage electrodes divided in a channel direction.

FIG. 8 is a schematic diagram showing a change in voltage when a large flux of X-rays enters an X-ray detection layer including high voltage electrodes 72 divided in the channel direction. As shown in FIG. 8, when the high voltage electrode 72 is divided in the channel direction, both the first and second partial electrodes 721 and 722 are located in the same row direction. It is thus unlikely that a large flux of X-rays enters only one of the first and second partial electrodes 721 and 722. When a large flux of X-rays enters both the first and second partial electrodes 721 and 722, a voltage drops in both the first and second partial electrodes 721 and 722, with the result that no voltage difference occurs between the first and second partial electrodes 721 and 722 to prevent an arc discharge from being generated.

As described above, an arc discharge can be prevented from being generated even when a large flux step is caused by dividing the high voltage electrode 72 in the channel direction. This makes it possible to reduce or prevent failures of the detector modules 51 and the high voltage electrodes 72.

Note that the mode of dividing the high voltage electrode 72 is not limited to the above. If the high voltage electrode 72 is divided at least in the channel direction, an arc discharge due to a flux step can be reduced.

Figure 9:
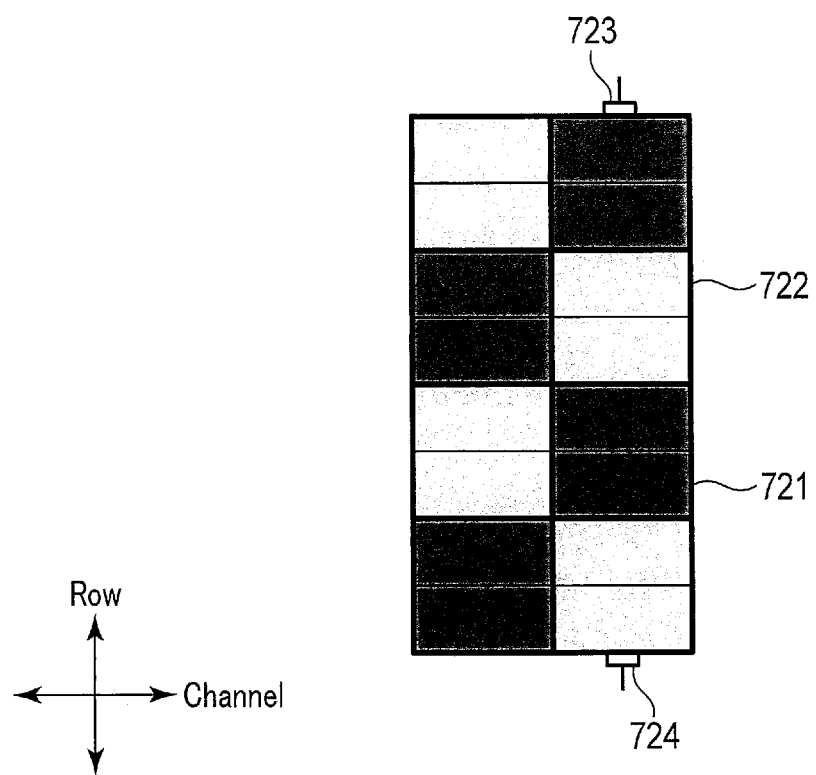
FIG. 9 is a diagram showing an example of an X-ray detection layer including high voltage electrodes divided in a checkerboard pattern.

FIG. 9 is a diagram showing an example of an X-ray detection layer including high voltage electrodes 72 divided in a checkerboard pattern. As shown in FIG. 9, the high voltage electrodes 72 include first partial electrodes 721 and second partial electrodes 722 which are alternately divided in both the channel and row directions. The first partial electrodes 721 are connected to each other via signal lines (not shown), as are the second partial electrodes 722. In FIG. 9, two detector pixels or pixel electrodes are shown in the channel direction, but actually three or more detector pixels or pixel electrodes are arranged in the channel direction. Accordingly, the first and second partial electrodes 721 and 722 are arranged alternately in the channel direction. Furthermore, in FIG. 9, the number of detector pixels or pixel electrodes covered with one first partial electrode 721 and one second partial electrode 722 is two in the row direction and one in the channel direction, but the combination of the number in the row direction and the number in the channel direction is not particularly limited.

Since the high voltage electrode 72 having a checkerboard pattern is divided in the channel direction, both the first and second partial electrodes 721 and 722 are arranged in the same row direction. It is unlikely that a large flux of X-rays enters only one of the first and second partial electrodes 721 and 722. Thus, even when a flux step is caused in the row direction, it is unlikely that a large flux of X-rays enters only one of the first and second partial electrodes 721 and 722. Since, furthermore, the high voltage electrode 72 having a checkerboard pattern is also divided in the row direction, both the first and second partial electrodes 721 and 722 are arranged in the same channel direction position. Thus, even when a flux step is caused in the channel direction, it is unlikely that a large flux of X-rays enters only one of the first and second partial electrodes 721 and 722. Therefore, an arc discharge can be further prevented from being generated and accordingly the failures of the detector modules 51 and the high-voltage electrodes 72 can be further reduced or prevented.

Second Embodiment

Below is a description of an X-ray computed tomography apparatus according to a second embodiment. This X-ray computed tomography apparatus controls the power to a high voltage electrode 72 to reduce an arc discharge. Note that the mode of dividing the high voltage electrode 72 according to the second embodiment is not particularly limited, but can be applied to any of the division in the channel direction, the division in the row direction, and the division in both the channel and row directions.

Example 1

Figure 10:
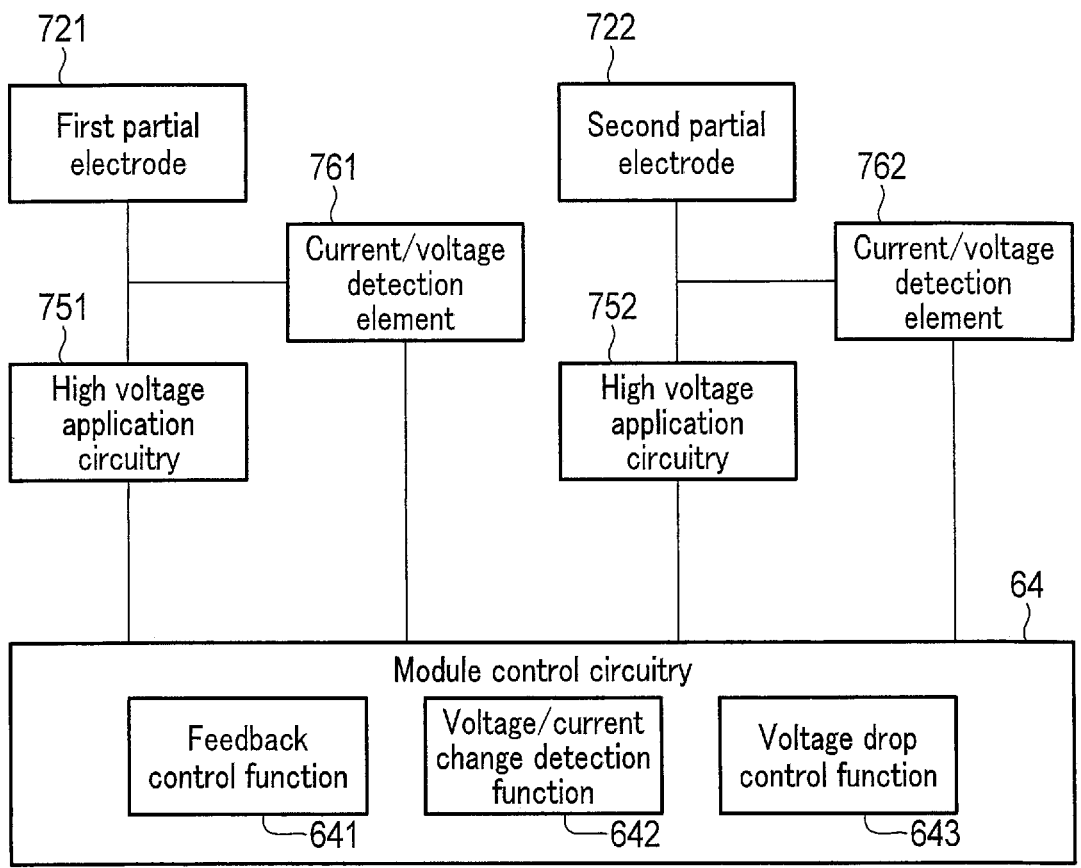
FIG. 10 is a block diagram showing a configuration example of a power control system related to a high voltage electrode according to example 1 of a second embodiment.

FIG. 10 is a block diagram showing a configuration example of a power control system related to a high voltage electrode 72 according to example 1 of the second embodiment. As shown in FIG. 10, a module control circuitry 64 performs a feedback control function 641, a voltage/current change detection function 642 and a voltage drop control function 643.

In the feedback control function 641, the module control circuitry 64 controls high voltage application circuitry 751 and 752 to apply a high voltage to partial electrodes 721 and 722 independently of each other. Specifically, the module control circuitry 64 applies a high voltage with a set value to a first partial electrode 721 under the control of feedback based on a detected current/detected voltage from a current/voltage detection element 761 and a target current/target voltage. Similarly, the module control circuitry 64 applies a high voltage with a set value to a second partial electrode 722 under the control of feedback based on a detected current/detected voltage from a current/voltage detection element 762 and a target current/target voltage. The set values of voltages applied to the first and second partial electrodes 721 and 722 are set to the same value. In addition, the module control circuitry 64 can control high voltage application circuitry 751 and 752 to switch the polarity of the high voltage applied to the partial electrodes 721 and 722.

In the voltage/current change detection function 642, the module control circuitry 64 detects the incidence of a predetermined flux of X-rays upon either one of the first and second partial electrodes 721 and 722. The predetermined flux is set to cause a voltage to drop such that an arc discharge occurs when the flux of X-rays enters a semiconductor crystal 71. The module control circuitry 64 according to example 1 detects a change in the detected current/detected voltage from the current/voltage detection element 762. More specifically, the module control circuitry 64 detects an increase in the detected current or a decrease in the detected voltage.

In the voltage drop control function 643, when the module control circuitry 64 detects that a predetermined flux of X-rays has entered either one of the first and second partial electrodes 721 and 722, it controls a high voltage applied to the first and second partial electrodes 721 and 722. When the module control circuitry 64 detects a change in the detected current/detected voltage by the voltage/current change detection function 642, it drops a high voltage applied to partial electrode 722 and 721 other than the partial electrodes 721 and 722 in which the change in the detected current/detected voltage is detected.

FIG. 11 is a diagram showing an example of high voltage control performed by voltage monitoring according to example 1. Assume that a large flux of X-rays enters a semiconductor crystal region corresponding to the first partial electrode 721 at time T1 as shown in FIG. 11. In this case, the voltage applied to the first partial electrode 721 starts to drop and accordingly the voltage of the first partial electrode 721 detected by the current/voltage detection element 761 also drops. The module control circuitry 64 detects the drop of the detected voltage by the voltage/current change detection function 642 to detect the drop of the voltage applied to the first partial electrode 721. The drop of the detected voltage has only to be detected by comparing a difference in detected voltage per unit time and a threshold value, comparing a time differential value of the detected voltage and a threshold value, and the like.

When the module control circuitry 64 detects the drop of the detected voltage, it controls the high voltage application circuitry 752 by the voltage drop control function 643 to lower the voltage applied to the second partial electrode 722. In FIG. 11, start time T2 of the control of the voltage drop is later than detection time T1 of the drop of the voltage applied to the first partial electrode 721, but the start time T2 may coincide with the detection time T1. In controlling the voltage drop, the module control circuitry 64 feedback-controls the high voltage application circuitry 752 so that the voltage applied to the second partial electrode 722 drops with a time change similar to the drop of the voltage applied to the first partial electrode 721. For example, the module control circuitry 64 sets a target voltage to allow the voltage applied to the second partial electrode 722 to drop following the detected voltage of the first partial electrode 721 and with a time change similar to the drop of the voltage applied to the first partial electrode 721.

As described above, according to example 1, the module control circuitry 64 lowers the voltage applied to the second partial electrode 722 when it detects the drop of the voltage applied to the first partial electrode 721 while regarding an event of drop of the voltage applied to the first partial electrode 721 as an event of incidence of a large flux of X-rays. Even though a voltage drop occurs in the first partial electrode 721 due to the incidence of a large flux of X-rays, it is unlikely that a difference in voltage between the first and second partial electrodes 721 and 722 is so large as to generate an arc discharge because the voltage drop also occurs artificially in the second partial electrode 722. In addition, the voltage applied to the second partial electrode 722 is caused to drop with a time change similar to the drop of the voltage applied to the first partial electrode 721 to allow the difference in voltage between the first and second partial electrodes 721 722 to be narrowed further. The arc discharge can thus be prevented from being generated.

FIG. 12 is a diagram showing an example of high voltage control performed by current monitoring according to example 1. As shown in FIG. 12, when a large flux of X-rays enters a semiconductor crystal region corresponding to the first partial electrode 721 at time T1, the current supplied to the first partial electrode 721 starts to rise and accordingly the current of the first partial electrode 721 detected by the current/voltage detection element 761 rises. The module control circuitry 64 detects the rise of the detected current by the voltage/current change detection function 642 to detect the drop of the voltage applied to the first partial electrode 721. The rise of the detected current has only to be detected by comparing a difference in detected current per unit time and a threshold value, comparing a time differential value of the detected current and a threshold value, and the like.

When the module control circuitry 64 detects the rise of the detected current, it controls the high voltage application circuitry 752 by the voltage drop control function 643 at time T2 to lower the voltage applied to the second partial electrode 722. As described above, in the high voltage control by current monitoring, the module control circuitry 64 lowers the voltage applied to the second partial electrode 722 when it detects the rise of the current supplied to the first partial electrode 721 while regarding an event of rise of the current supplied to the first partial electrode 721 as an event of incidence of a large flux of X-rays. Even though a voltage drop occurs in the first partial electrode 721 due to the incidence of a large flux of X-rays, it is unlikely that a difference in voltage between the first and second partial electrodes 721 and 722 is so large as to generate an arc discharge because the voltage drop also occurs artificially in the second partial electrode 722. The arc discharge can thus be prevented from being generated.

Example 2

Figure 13:
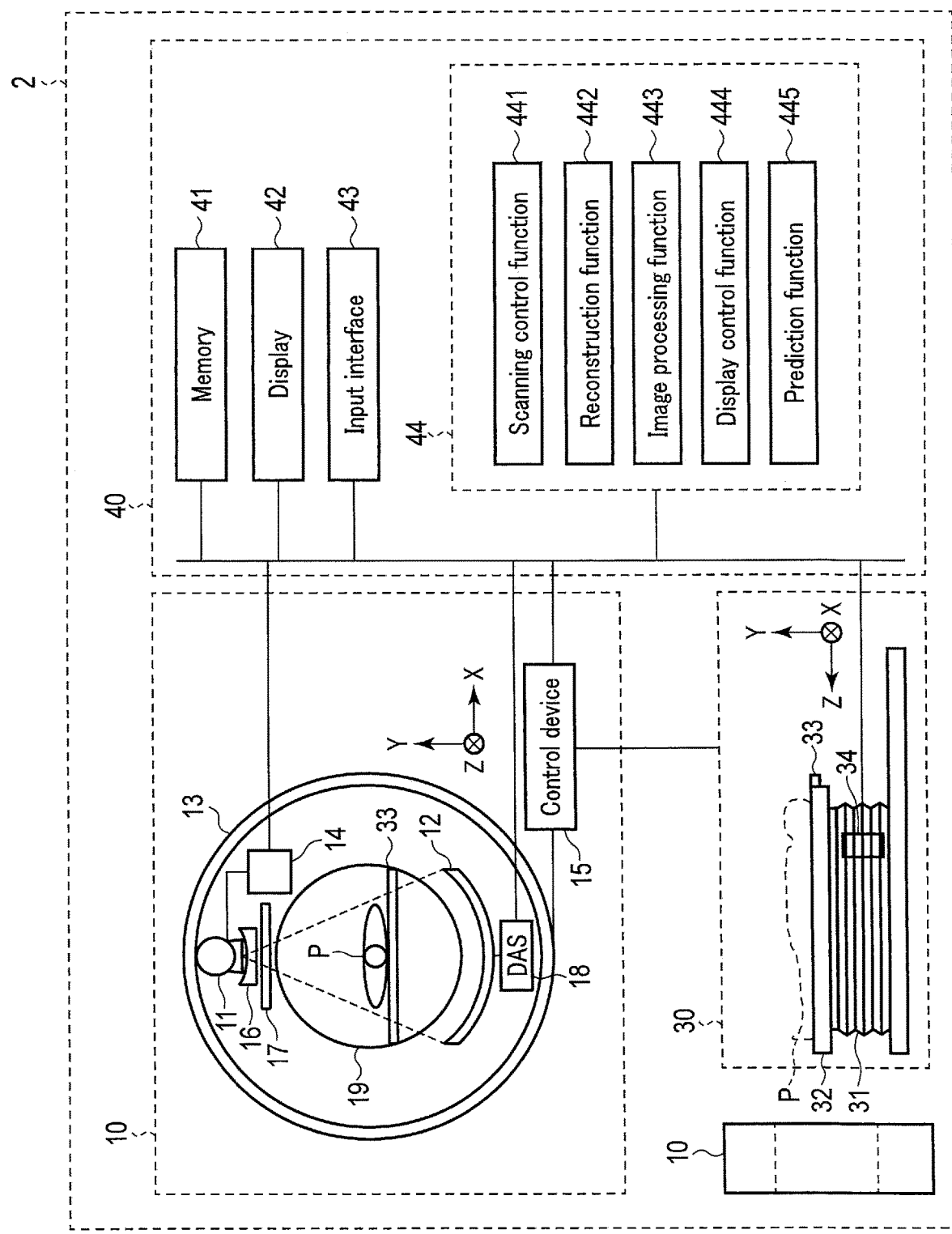
FIG. 13 is a diagram showing a configuration example of an X-ray computed tomography apparatus according to example 2 of the second embodiment.

FIG. 13 is a diagram showing a configuration example of an X-ray computed tomography apparatus 2 according to example 2 of the second embodiment. As shown in FIG. 13, the processing circuitry 44 of the X-ray computed tomography apparatus 2 performs a prediction function 445 in addition to the shooting control function 441, reconstruction function 442, image processing function 443 and display control function 444.

In the prediction function 445, based on scan planning, the processing circuitry 44 predicts time when a predetermined flux of X-rays enters. The predetermined flux is set to cause a voltage drop so as to generate an arc discharge when X-rays of the flux enter the semiconductor crystal 71. Specifically, the processing circuitry 44 uses a positioning image generated in the scan planning. As the positioning image, an X-ray image generated based on projection data collected by positioning scanning is used. The positioning scanning is a method for performing X-ray scanning on subject P while the X-ray tube 11 is fixed at an angle of 0°, 90°, 180°, 270° and the like. Based on the range occupied by a subject region in the positioning image, the processing circuitry 44 predicts time when a predetermined flux of X-rays enters each of the detector pixels 70. Based on two or more positioning images with different angles, the time when a predetermined flux of X-rays enters each of the detector pixels 70 may be predicted. The time may be specified by time elapsed from the scanning start time, by the number of views from the scanning start time, or by the absolute time. Hereinafter, the predicted time will be referred to as large-flux incidence prediction time.

Note that the large-flux incidence prediction time need not be strictly predicted for each of the detector pixels 70 included in each of the detector modules 51, but has only to be predicted in units of the same partial electrodes 721 and 722. When the large-flux incidence prediction time varies among a plurality of detector pixels 70 belonging to the same partial electrodes 721 and 722, the earliest time has only to be set to the large-flux incidence prediction time for the partial electrodes 721 and 722.

FIG. 14 is a diagram showing a configuration example of a power control system related to a high voltage electrode according to example 2 of the second embodiment. As shown in FIG. 14, the module control circuitry 64 performs a prediction time detection function 644 in addition to the feedback control function 641 and the voltage drop control function 643.

In the prediction time detection function 644, the module control circuitry 64 detects that a predetermined flux of X-rays enters one of the first and second partial electrodes 721 and 722. The module control circuitry 64 according to example 2 detects that the large-flux incidence prediction time predicted by the prediction function 445 has been arrived. In the voltage drop control function 643, the module control circuitry 64 lowers a high voltage applied to the other partial electrode 721 or 722 when it detects that the large-flux incidence prediction time has been arrived.

FIG. 15 is a diagram showing an example of high voltage control according to example 2. Assume that time T4 is set to the large-flux incidence prediction time for the detector pixel 70 corresponding to the first partial electrode 721 as shown in FIG. 15. Note that the large-flux incidence prediction time for the detector pixel 70 corresponding to the second partial electrode 722 is later or no longer than time T4.

At time T4, the module control circuitry 64 detects in the prediction time detection function 644 that the large-flux incidence prediction time has been arrived. In this case, the voltage applied to the first partial electrode 721 starts to drop.

At time T5 after time T4, in the voltage drop control function 643, the module control circuitry 64 controls the high voltage application circuitry 752 to lower the voltage applied to the second partial electrode 722. In FIG. 15, time T5 when the voltage drop control starts is later than time T4 when the large-flux incidence prediction time is arrived, but time T5 may coincide with time T4. In the voltage drop control, the module control circuitry 64 feedback-controls the high voltage application circuitry 752 such that the voltage applied to the second partial electrode 722 drops with a time change similar to the drop of the voltage applied to the first partial electrode 721.

As described above, according to example 2, when the module control circuitry 64 detects that the large-flux incidence prediction time is arrived, it lowers the voltage applied to the second partial electrode 722 while regarding an event of arrival of the large-flux incidence prediction time as an event of incidence of a large-flux of X-rays upon the first partial electrode 721. Even though a voltage drop occurs in the first partial electrode 721 due to the incidence of a large flux of X-rays, it is unlikely that a difference in voltage between the first and second partial electrodes 721 and 722 is so large as to generate an arc discharge because the voltage drop also occurs artificially in the second partial electrode 722. In addition, the voltage applied to the second partial electrode 722 is caused to drop with a time change similar to the drop of the voltage applied to the first partial electrode 721 to allow the difference in voltage between the first and second partial electrodes 721 722 to be narrowed further. The arc discharge can thus be prevented from being generated.

Example 3

The processing circuitry 44 according to example 3 performs a prediction function 445 in addition to the shooting control function 441, reconstruction function 442, image processing function 443 and display control function 444. In the prediction function 445, the processing circuitry 44 predicts time (large-flux incidence prediction time) when a predetermined flux of X-rays enters based on scan planning, as in the case of example 2. Then, the processing circuitry 44 specifies time which is before the large-flux incidence prediction time by a predetermined time. The predetermined time corresponds to time for supplying charges from a capacitor element (described later) to the partial electrodes 721 and 722. Hereinafter, the specified time will be referred to as storage start time.

Figure 16:
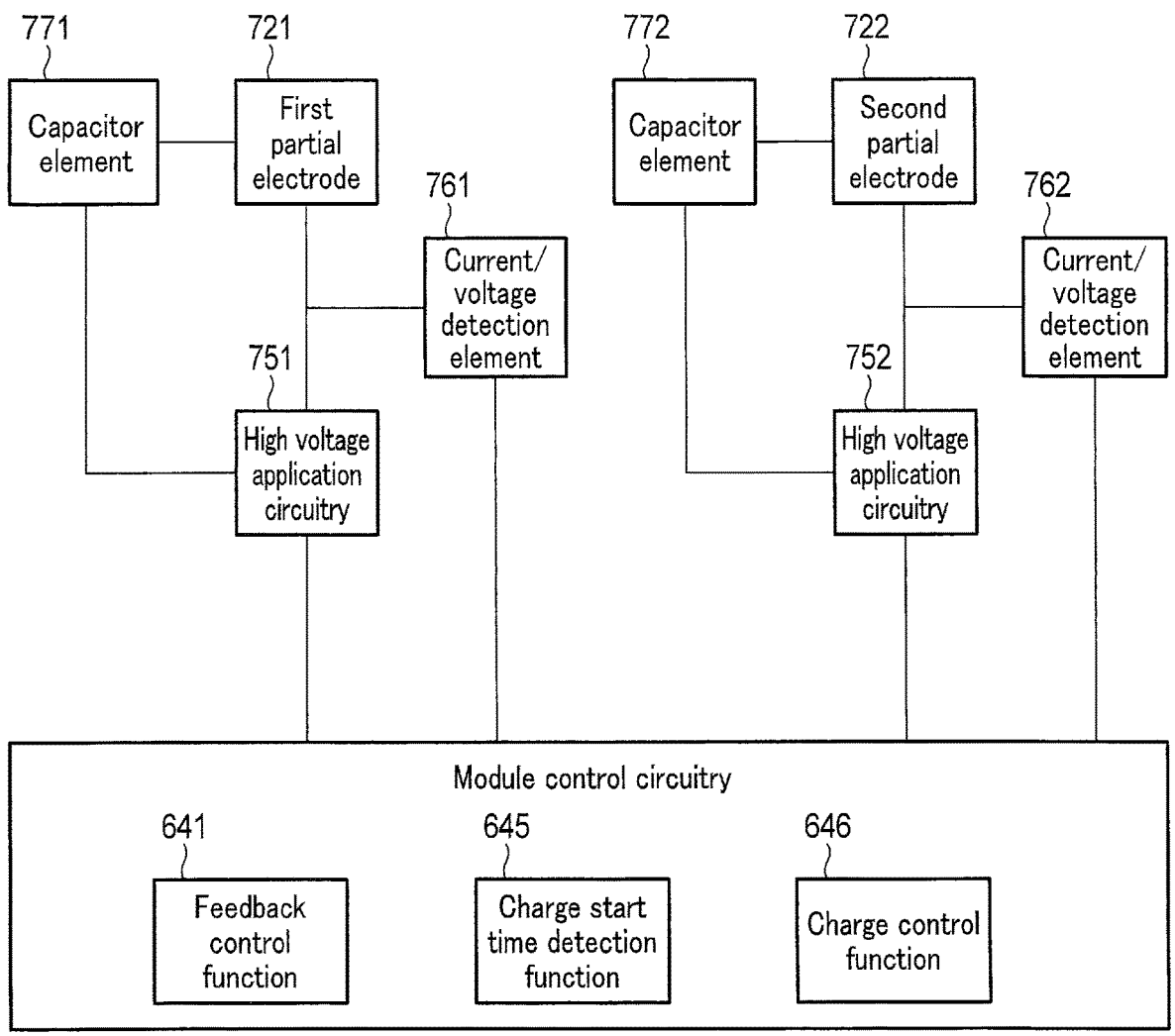
FIG. 16 is a block diagram showing a configuration example of a power control system related to a high voltage electrode according to example 3 of the second embodiment.

FIG. 16 is a block diagram showing a configuration example of a power control system related to a high voltage electrode according to example 3 of the second embodiment. As shown in FIG. 16, a capacitor element 771 is provided between the first partial electrode 721 and the high voltage application circuitry 751. The capacitor element 771 is a circuitry element which stores charges by a supply of power from the high voltage application circuitry 751. The charges stored in the capacitor element 771 are supplied to the first partial electrode 721 when there is a shortage of charges in the semiconductor crystal region that is in contact with the first partial electrode 721. Similarly, a capacitor element 772 is provided between the second partial electrode 722 and the high voltage application circuitry 752. The capacitor element 772 is a circuitry element which stores charges by a supply of power from the high voltage application circuitry 752. The charges stored in the capacitor element 772 are supplied to the second partial electrode 722 when there is a shortage of charges in the semiconductor crystal region that is in contact with the second partial electrode 722. As the capacitor elements 771 and 772, for example, capacitors are suitable.

The module control circuitry 64 performs a charge start time detection function 645 and a charge control function 646 in addition to the feedback control function 641. In the charge start time detection function 645, the module control circuitry 64 detects that a predetermined flux of X-rays enters either one of the first and second partial electrodes 721 and 722. The module control circuitry 64 according to example 3 detects that the charge start time specified by the prediction function 445 has been arrived. In the charge control function 646, when the module control circuitry 64 detects that the large-flux incidence prediction time has been arrived, it controls the high voltage application circuitry 751 or 752 so as to store charges in the capacitor element 771 or 772 connected to the other partial electrode.

FIG. 17 is a diagram showing an example of high voltage control according to example 3 of the second embodiment. Assume that time T7 is set to the large-flux incidence prediction time for the detector pixel 70 corresponding to the first partial electrode 721, and time T6 before time T7 is set to the charge start time for the capacitor element 771. Note that the charge start time for the detector pixel 70 corresponding to the second partial electrode 722 is later or no longer than time T6.

At time T6, the module control circuitry 64 detects the arrival of the charge start time by the storage start time detection function 645. When the module control circuitry 64 detects the arrival of the charge start time, it controls the high voltage application circuitry 752 by the storage control function 646 to start to store charges in the storage element 771. At time T7, a large flux of X-rays enters the first partial electrode 721. Accordingly a number of charges are generated in the semiconductor crystal 71, and the charges are supplied from the capacitor element 771 to compensate for the shortage of current supply to the semiconductor crystal 71 by the high voltage electrode 72. The voltage of the first partial electrode 721 can thus be prevented from dropping. It is therefore possible to prevent a voltage difference from occurring between the first and second partial electrodes 721 and 722 so as to generate an arc discharge.

Third Embodiment

The X-ray computed tomography apparatus according to a third embodiment prevents an arc discharge from being generated by a difference in voltage between detector modules 51 when a large flux of X-rays enters.

FIG. 18 is a diagram showing an example of arrangement of the detector modules 51 according to the third embodiment. As shown in FIG. 18, the detector modules 51 are arranged side by side in the channel direction. A spacer 58 is provided between adjacent detector modules 51. The spacer 58 may be formed of an insulating material or a non-insulating material.

Figure 19:
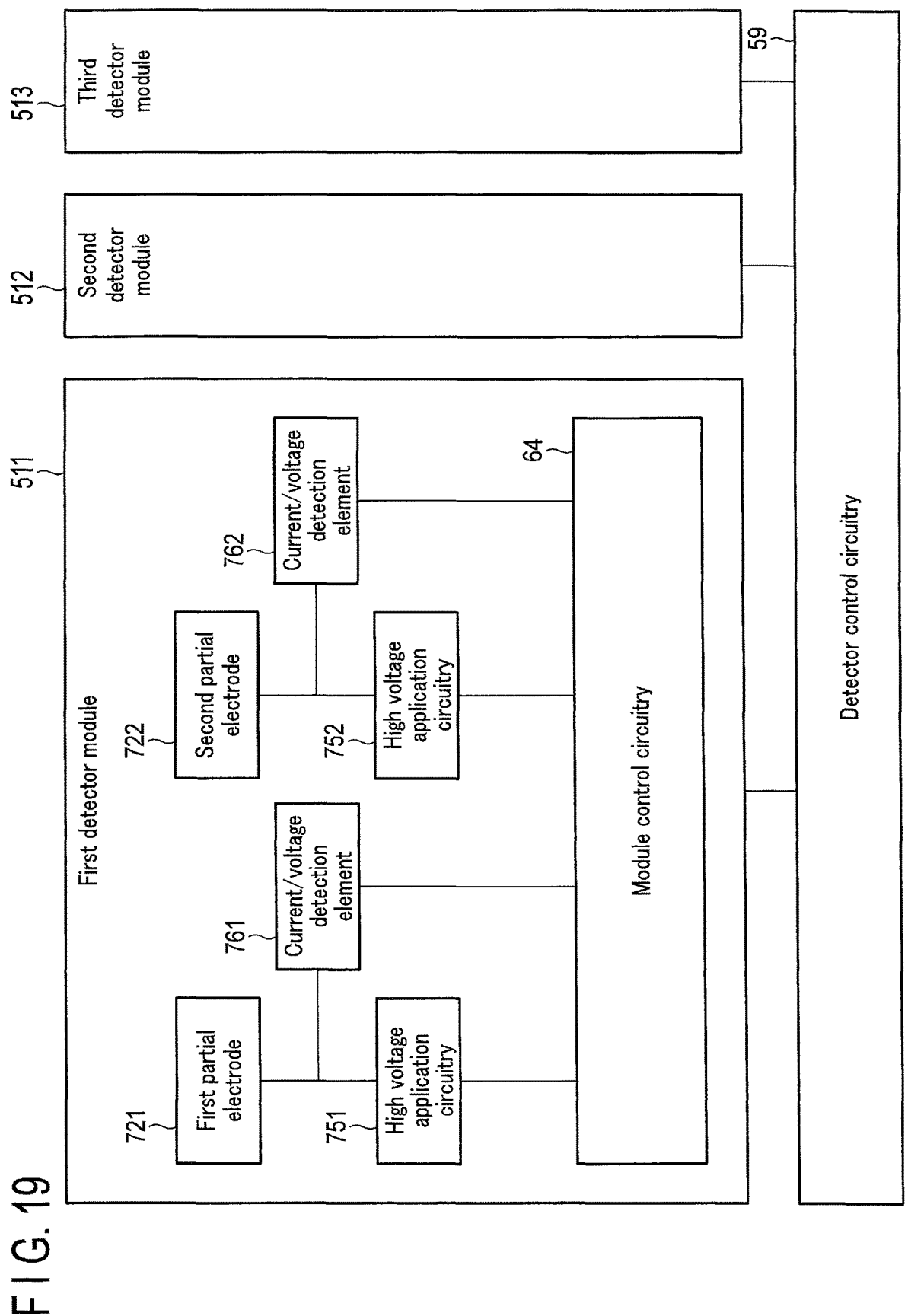
FIG. 19 is a block diagram showing a configuration example of a power control system related to the detector modules according to the third embodiment.

FIG. 19 is a block diagram showing a configuration example of a power control system related to the detector module 51. FIG. 19 illustrates three detector modules 51 of a first detector module 511, a second detector module 512 and a third detector module 513, but four or more detector modules 51 may be provided. In the following description, the first, second and third detector modules 511, 512 and 513 will be referred to as the detector modules 51 if they are not distinguished.

As shown in FIG. 19, each of the detector modules 51 includes a power control system as described in some of the foregoing examples. A detector control circuitry 59 is connected to each of the detector modules 51.

The detector control circuitry 59 is a control circuitry that integrally controls the high voltage control of each of the detector modules 51. The detector control circuitry 59 detects that a predetermined flux of X-rays enters one of the detector modules 51. When the detector control circuitry 59 detects that a predetermined flux of X-rays enters, it controls a high voltage applied to one of the detector modules 51 which is adjacent to another one.

Figure 20:
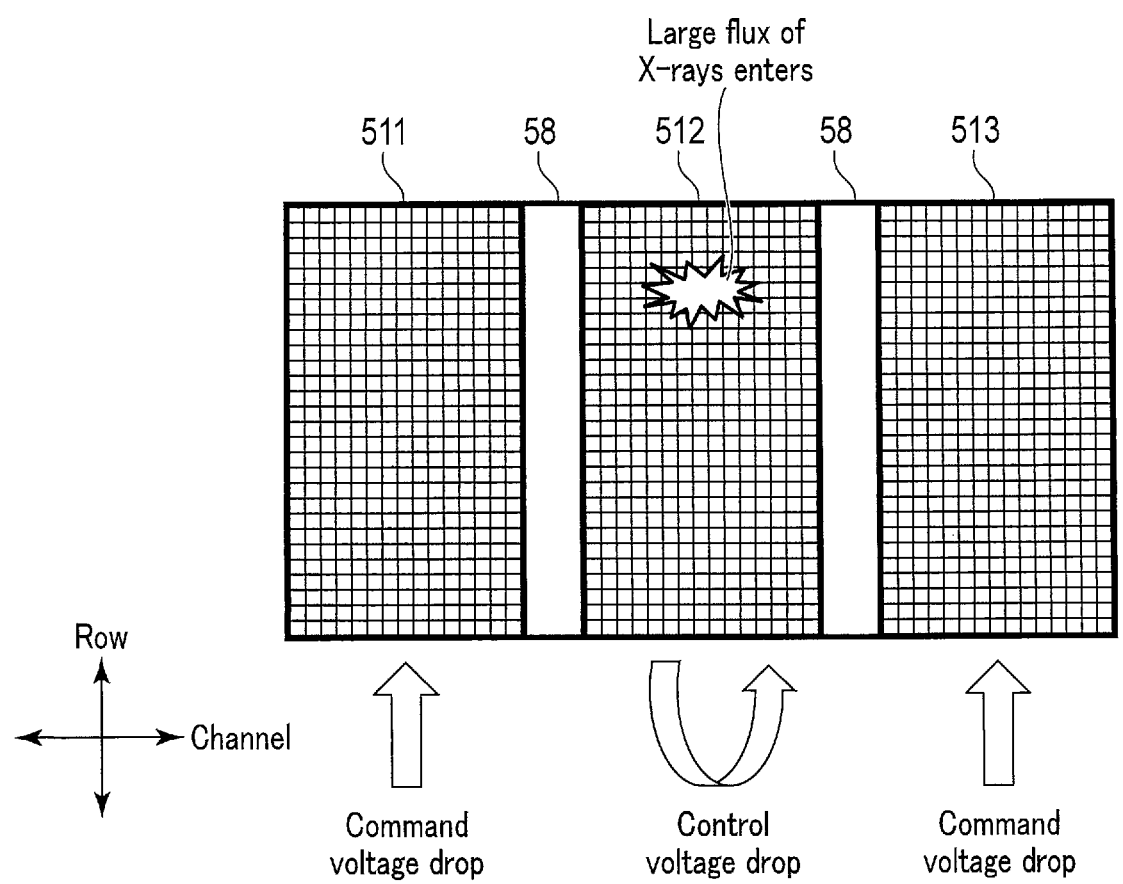
FIG. 20 is a schematic diagram showing an example of high voltage control according to the third embodiment.

FIG. 20 is a schematic diagram showing an example of high voltage control according to the third embodiment. Assume that a large flux of X-rays enters the second detector module 512 as shown in FIG. 20. In this case, the second detector module 512 controls a voltage drop to lower the voltages of both the first and second partial electrodes 721 and 722 as in some of the examples described above. At this time, the second detector module 512 transmits to the detector control circuitry 59 an electrical signal indicating that a large flux of X-rays has entered (hereinafter referred to as an incident signal). The incident signal is generated due to the facts that a voltage drop occurs in the high voltage electrode 72, an arc discharge is generated, a detected current rises above a threshold value, a detected voltage drops below a threshold value, a large flux incidence time is arrived, and the like.

Upon receiving an incident signal from the second detector module 512, the detector control circuitry 59 supplies an electrical signal (hereinafter referred to as a command signal) indicating a voltage drop to a detector module 51 adjacent to the detector module 51 that has transmitted the incident signal. For example, when the detector control circuitry 59 receives an incident signal from the second detector module 512, it supplies a command signal to the first and third detector module 511 and 513. The detector module 51 supplied with the command signal controls the high voltage application circuitry 751 and 752 to lower the voltages of the first and second partial electrodes 721 and 722.

According to the above high voltage control, when a large flux of X-rays enters the second detector module 512 to cause a voltage drop, a voltage drop is also artificially caused in the first and third detector modules 511 and 513 which are adjacent to the second detector module 512. This makes it possible to prevent an arc discharge from being generated due to a difference in voltage between the detector modules 51.

Others

The configurations described in the above embodiments are exemplary and, for example, the module control circuitry 64 and the detector control circuitry 59 may be provided in any of the components included in the X-ray computed tomography apparatus. For example, in the above embodiments, the module control circuitry 64 is provided in the detector module 51. However, the module control circuitry 64 may be provided on the control board or the like of the X-ray detection device 50, on the control device 15 of the gantry 10, or on the processing circuitry 44 or the like of the console 40. Similarly, in the above embodiments, the detector control circuitry 59 is provided in the X-ray detector 50 it may be provided in the module control circuitry 64 or the like of the detector module 51, may be provided in the control device 15 of the frame 10, or may be provided in the processing circuitry 44 or the like of the console 40.

In the above embodiments, the high voltage electrode 72 is divided into two types of partial electrodes of a first partial electrode 721 and a second partial electrode 722. However, none of the embodiments is limited to this division. For example, the high voltage electrode 72 may be divided into three or more types of partial electrodes to which a high voltage can be applied, the partial electrodes being independently of each other.

In the above embodiments, the radiation detector was assumed to be an X-ray detector that detects X-rays. However, the object of detection of the radiation detector according to the present embodiments is not limited to X-rays, and any electromagnetic radiation and particle radiation such as gamma rays, electron rays, proton rays, and neutron rays can be used. The radiation detector according to the present embodiments can be applied to a detector that detects these radiations.

According to at least one of the embodiments described above, an arc discharge can be prevented from being generated.

The wording "processor" used in the above description means a CPU, a GPU, or a circuitry such as an application specific integrated circuitry (ASIC), a programmable logic device (e.g., a simple programmable logic device (SPLD)), a complex programmable logic device (CPLD) and a field programmable gate array (FPGA). The processor implements a function by reading a program stored in the storage circuitry. Instead of storing a program in the storage circuitry, the program may be incorporated directly into the circuitry of the processor. In this case, the processor implements a function by reading the program from the circuitry. Furthermore, instead of executing a program, a function corresponding to the program may be implemented by combining logic circuitry. Note that each of the processors of the present embodiments is configured not only as a single circuitry, but also as a single processor of the combination of a plurality of independent circuitry to implement its function. In addition, a plurality of components shown in FIGS. 1, 6, 10, 13, 14, 16 and 19 may be integrated into one processor to implement its function.

While certain embodiments have been described, these embodiments have been presented by way of example only, and are not intended to limit the scope of the inventions. Indeed, the novel embodiments described herein may be embodied in a variety of other forms; furthermore, various omissions, substitutions, changes and combinations of the embodiments described herein may be made without departing from the spirit of the inventions. The accompanying claims and their equivalents are intended to cover such forms or modifications as would fall within the scope and spirit of the inventions.

With respect to the above embodiments, the following clauses are disclosed as one aspect and optional features of the invention.

(1)

A detector module comprises:

a direct-conversion semiconductor crystal;

a first electrode provided on a first surface side of the semiconductor crystal; and a plurality of second electrodes provided on a second surface side of the semiconductor crystal opposite to the first electrode with the semiconductor crystal therebetween, and the first electrode includes a first partial electrode and a second partial electrode which are applied with a high voltage independently of each other and divided at least in a channel direction.

Wherein the first surface may be a surface of incidence of radiation. For example, the radiation may be X-rays output from an X-ray tube.

(2)

The detector module according to clause 1, wherein the first electrode may not be divided into the first partial electrode or the second partial electrode in a row direction orthogonal to the channel direction.

(3)

The detector module according to clause 1, wherein the first electrode may be further divided into the first partial electrode and the second partial electrode in a row direction orthogonal to the channel direction.

(4)

The detector module according to clause 3, wherein the first partial electrode and the second partial electrode may be arranged alternately in the channel direction and the row direction.

(5)

The detector module of any of clauses 1 to 4, may further comprise a high voltage application unit which applies a high voltage to the first partial electrode and the second partial electrode independently.

(6)

A detector module comprises:

a direct-conversion semiconductor crystal;

a first electrode provided on a first surface side of the semiconductor crystal and including a first partial electrode and a second partial electrode which are applied with a high voltage independently of each other and divided in a channel direction and/or a row direction;

a plurality of second electrodes provided on a second surface side of the semiconductor crystal opposite to the first electrode with the semiconductor crystal therebetween; and control circuitry which detects incidence of a predetermined flux of radiation upon the first partial electrode to control a high voltage applied to the second partial electrode.

Wherein the first surface may be a surface of incidence of radiation. For example, the radiation may be X-rays output from an X-ray tube.

(7)

The detector module according to clause 6, wherein the control circuitry may detect a rise of current supplied to the first partial electrode in order to detect the incidence of a predetermined flux of radiation, and may lower a high voltage applied to the second partial electrode when the rise of current is detected.

(8)

The detector module according to clause 6, wherein the control circuitry may detect a drop of a high voltage applied to the first partial electrode in order to detect the incidence of a predetermined flux of radiation, and may lower a high voltage applied to the second partial electrode when the drop of a high voltage is detected.

(9)

The detector module according to clause 6, wherein the control circuitry may detect that the incidence of a predetermined flux of radiation has been arrived at prediction time, based on scan planning in order to detect the incidence of a predetermined flux of radiation, and may lower a high voltage applied to the second partial electrode when the arrival at the prediction time is detected.

(10)

The detector module according to clause 6, the control circuitry may detect that the incidence of a predetermined flux of radiation has been arrived at second prediction time before first prediction time, based on scan planning in order to detect that the incidence of a predetermined flux of radiation, and may store charges in a capacitor element connected to the second partial electrode when the arrival at the second prediction time is detected.

(11)

An X-ray computed tomography apparatus comprises:

an X-ray tube which generates X-rays; and an X-ray detector which detects the X-rays generated from the X-ray tube, and the X-ray detector includes:
a direct-conversion semiconductor crystal;
a first electrode provided on a first surface side of the semiconductor crystal; and
a plurality of second electrodes provided on a second surface side of the semiconductor crystal opposite to the first electrode with the semiconductor crystal therebetween, and
the first electrode includes a first partial electrode and a second partial electrode which are applied with a high voltage independently of each other and divided at least in a channel direction.

Wherein the first surface may be a surface of incidence of radiation. For example, the radiation may be X-rays output from an X-ray tube.

(12)

An X-ray computed tomography apparatus comprises:
an X-ray tube which generates X-rays;
an X-ray detector which detects the X-rays generated from the X-ray tube, the X-ray detector including a direct-conversion semiconductor crystal, a first electrode provided on a first surface side of the semiconductor crystal and including a first partial electrode and a second partial electrode which are applied with a high voltage independently of each other and divided in a channel direction and/or a row direction, and a plurality of second electrodes provided on a second surface side of the semiconductor crystal opposite to the first electrode with the semiconductor crystal therebetween; and
control circuitry which detects incidence of a predetermined flux of X-rays upon the first partial electrode to control a high voltage applied to the second partial electrode.

Wherein the first surface may be a surface of incidence of radiation. For example, the radiation may be X-rays output from an X-ray tube.

(13)

An X-ray computed tomography apparatus comprises:
an X-ray tube which generates X-rays;
an X-ray detector which detects the X-rays generated from the X-ray tube and includes a plurality of detector modules which are applied with a high voltage independently of each other and arranged in a channel direction and/or a row direction; and
control circuitry which detects incidence of a predetermined flux of X-rays upon a first module among the detector modules to control a high voltage applied to a second module among the detector modules.

(14)

An X-ray detection device comprises:
a plurality of detector modules which detect X-rays and which are applied with a high voltage independently of each other and arranged in a channel direction and/or a row direction; and
control circuitry which detects incidence of a predetermined flux of X-rays upon a first module among the detector modules to control a high voltage applied to a second module among the detector modules.

The invention claimed is:

1. A detector module comprising:
a direct-conversion semiconductor crystal;
a first electrode provided on a first surface side of the semiconductor crystal; and
a plurality of second electrodes provided on a second surface side of the semiconductor crystal opposite to the first electrode with the semiconductor crystal therebetween, wherein
the first electrode includes a first partial electrode and a second partial electrode which are applied with a high voltage independently of each other and divided at least in a channel direction, and
each of the second electrodes faces the first partial electrode or the second partial electrode.

2. The detector module of claim 1, wherein the first electrode is not divided into the first partial electrode or the second partial electrode in a row direction orthogonal to the channel direction.

3. The detector module of claim 1, wherein the first electrode is further divided into the first partial electrode and the second partial electrode in a row direction orthogonal to the channel direction.

4. The detector module of claim 3, wherein the first partial electrode and the second partial electrode are arranged alternately in the channel direction and the row direction.

5. The detector module of claim 1, further comprising a high voltage application unit which applies a high voltage to the first partial electrode and the second partial electrode independently.

6. A detector module comprising:
a direct-conversion semiconductor crystal;
a first electrode provided on a first surface side of the semiconductor crystal and including a first partial electrode and a second partial electrode which are applied with a high voltage independently of each other and divided in a channel direction and/or a row direction;
a plurality of second electrodes provided on a second surface side of the semiconductor crystal opposite to the first electrode with the semiconductor crystal therebetween; and
control circuitry which detects incidence of a predetermined flux of radiation upon the first partial electrode to control a high voltage applied to the second partial electrode, wherein
each of the second electrodes faces the first partial electrode or the second partial electrode.

7. The detector module of claim 6, wherein the control circuitry detects a drop of a high voltage applied to the first partial electrode in order to detect the incidence of a predetermined flux of radiation, and lowers a high voltage applied to the second partial electrode when the drop of a high voltage is detected.

8. The detector module of claim 6, wherein the control circuitry detects a rise of current supplied to the first partial electrode in order to detect the incidence of a predetermined flux of radiation, and lowers a high voltage applied to the second partial electrode when the rise of current is detected.

9. The detector module of claim 6, wherein the control circuitry detects that the incidence of a predetermined flux of radiation has been arrived at a prediction time, based on scan planning in order to detect the incidence of a predetermined flux of radiation, and lowers a high voltage applied to the second partial electrode when the arrival at the prediction time is detected.

10. The detector module of claim 6, wherein the control circuitry detects that the incidence of a predetermined flux of radiation has been arrived at a second prediction time before a first prediction time, based on scan planning in order to detect that the incidence of a predetermined flux of radiation, and stores charges in a capacitor element connected to the second partial electrode when the arrival at the second prediction time is detected.

11. An X-ray computed tomography apparatus comprising:
- an X-ray tube which generates X-rays; and
- an X-ray detector which detects the X-rays generated from the X-ray tube,
- the X-ray detector includes:
    - a direct-conversion semiconductor crystal;
    - a first electrode provided on a first surface side of the semiconductor crystal; and
    - a plurality of second electrodes provided on a second surface side of the semiconductor crystal opposite to the first electrode with the semiconductor crystal therebetween, wherein
- the first electrode includes a first partial electrode and a second partial electrode which are applied with a high voltage independently of each other and divided at least in a channel direction, and
- each of the second electrodes faces the first partial electrode or the second partial electrode.

* * * * *